US008852267B2

(12) United States Patent
Cattaneo

(10) Patent No.: US 8,852,267 B2
(45) Date of Patent: Oct. 7, 2014

(54) STENT WITH FLAPS

(75) Inventor: Giorgio Cattaneo, Karlsruhe (DE)

(73) Assignee: Acandis GmbH & Co., Pfinztal (DE)

( * ) Notice: Subject to any disclaimer, the term of this patent is extended or adjusted under 35 U.S.C. 154(b) by 0 days.

(21) Appl. No.: 13/519,106

(22) PCT Filed: Dec. 22, 2010

(86) PCT No.: PCT/EP2010/007888
§ 371 (c)(1),
(2), (4) Date: Sep. 10, 2012

(87) PCT Pub. No.: WO2011/076408
PCT Pub. Date: Jun. 30, 2011

(65) Prior Publication Data
US 2012/0323309 A1 Dec. 20, 2012

(30) Foreign Application Priority Data
Dec. 23, 2009 (DE) .......................... 10 2009 060 228

(51) Int. Cl.
*A61F 2/06* (2013.01)
*A61F 2/856* (2013.01)
*A61F 2/91* (2013.01)
*A61F 2/915* (2013.01)
*A61F 2/07* (2013.01)
*A61F 2/82* (2013.01)
*A61F 2/90* (2013.01)

(52) U.S. Cl.
CPC ......... *A61F 2/856* (2013.01); *A61F 2250/0013* (2013.01); *A61F 2002/823* (2013.01); *A61F 2/91* (2013.01); *A61F 2/915* (2013.01); *A61F 2/07* (2013.01); *A61F 2/90* (2013.01); *A61F 2002/91558* (2013.01)
USPC .......................................... 623/1.24; 623/1.13

(58) Field of Classification Search
USPC ....................................... 623/1.24, 1.35, 1.13
See application file for complete search history.

(56) References Cited

U.S. PATENT DOCUMENTS

| 6,261,305 | B1 | 7/2001 | Marotta et al. | |
|---|---|---|---|---|
| 6,695,876 | B1 * | 2/2004 | Marotta et al. | ............... 623/1.15 |
| 2004/0059406 | A1 * | 3/2004 | Cully et al. | ................... 623/1.11 |
| 2005/0096728 | A1 * | 5/2005 | Ramer | ......................... 623/1.15 |
| 2006/0259131 | A1 | 11/2006 | Molaei et al. | |
| 2007/0239261 | A1 * | 10/2007 | Bose et al. | .................... 623/1.15 |
| 2008/0114446 | A1 * | 5/2008 | Hartley et al. | ............... 623/1.13 |
| 2010/0106240 | A1 | 4/2010 | Duggal et al. | |
| 2010/0145380 | A1 | 6/2010 | Quandt et al. | |

FOREIGN PATENT DOCUMENTS

| DE | 10351949 | A1 | 6/2005 |
|---|---|---|---|
| WO | 2007117645 | A2 | 10/2007 |
| WO | 2008022799 | A2 | 2/2008 |
| WO | 2008057568 | A1 | 5/2008 |

* cited by examiner

*Primary Examiner* — David H Willse
*Assistant Examiner* — Tiffany Shipmon
(74) *Attorney, Agent, or Firm* — Brooks Kushman P.C.

(57) ABSTRACT

A medicinal device with a tubular wall made of webs which delimit the cells, and a flexible membrane which forms at least one flap which has a first end connected to at least one first web of a cell, and a free second end which is disposed opposite the first end in the longitudinal direction of the flap. The flap, in the closed position, extends along the tubular wall and at least partially closes the cells, and can be moved to an open position in which the flap is radially deviated in relation to the wall in order to open the cells in a valve-like manner.

19 Claims, 13 Drawing Sheets

STENT WITH FLAPS

CROSS-REFERENCE TO RELATED APPLICATION

This application is the U.S. national phase of PCT Appln. No. PCT/EP2010/007888 filed on Dec. 22, 2010, which claims priority to DE Patent Application No. 10 2009 060 228.3 filed on Dec. 23, 2009, the disclosures of which are incorporated in their entirety by reference herein.

The invention relates to a medical device, preferably a stent or flow diverter, or generally a vascular support. Such medical devices are generally known.

Medical devices of the aforementioned type are usually used in blood vessels or other cavities of the body. Other cavities that can be treated with devices of this kind are, for example, the esophagus, the intestines, the bile duct, the trachea, the ureter or the like. Medical devices of this kind are often used for the treatment of stenoses, i.e. constrictions of the blood vessels, in particular of the coronary vessels, the major arteries and/or the cerebral vessels. A further possible use of known medical devices of this kind is in the treatment of aneurysms, i.e. vascular dilations. In these, a blood vessel widens locally, as a result of which the vessel wall is greatly expanded and stressed in this area. There is a risk of the expanded vessel wall tearing, which can result in hemorrhaging.

Known vascular supports usually have a lattice structure, which can be compressed to a smaller cross-sectional diameter in order to introduce the vascular support into a blood vessel. The vascular support widens in the blood vessel, or the vascular support expands and exerts a radial force on the vessel wall. Vascular constrictions can be widened in this way. The expansion of the vascular support can take place by widening of a balloon on which the vascular support is mounted. For this purpose, the balloon is filled with a liquid via a catheter. Alternatively, the lattice structure of the vascular support can widen automatically. Such vascular supports usually comprise a shape-memory material which, at body temperature, adopts its original shape.

The lattice structure of the known vascular supports has cells or meshes, of which the size varies depending on the intended use. For coverage of aneurysms, for example, vascular supports are used whose lattice structure has a relatively small mesh size or cell size. This has the effect that the blood flow within the aneurysm is stopped or at least reduced, such that further loading of the vessel wall within the aneurysm is avoided. An alternative method of treatment of aneurysms is one in which individual thin wire elements are introduced into the aneurysm and curl up in a haphazard manner in the aneurysm and thus block the blood flow within the aneurysm. When wire elements of this kind, called coils, are used, there is a danger of the coils protruding at least partially from the aneurysm into the blood vessel and affecting the blood flow within the blood vessel, with the result that clots, in particular thrombi, can form within the blood vessel. The coils can even be swept out of the aneurysm and cause a vascular occlusion in blood vessels situated downstream. In order to avoid this, the blood vessel is first of all stabilized with a vascular support in the area of the aneurysm. Coils are then introduced into the aneurysm via the meshes or cells of the vascular support. The chosen size of the meshes of the vascular support is critical. Larger meshes make it easier to introduce the coils into the aneurysm, but they also allow individual coil portions to protrude into the blood vessel at the same time. In addition, the larger meshes also permit a flow of blood within the aneurysm. Conversely, smaller meshes of the vascular support make it more difficult to introduce coils into the aneurysm.

In the treatment of stenoses, particularly stenoses comprising a vulnerable plaque, known vascular supports likewise have disadvantages. A vulnerable plaque is an accumulation of fat particles and body cells within a blood vessel, which accumulation is covered by a thin vascular intima. The vulnerable plaque narrows the cross section of the blood vessel, with the result that the stenosis forms. When such a stenosis is widened by a vascular support with a lattice structure, there is a danger of the webs of the lattice structure damaging the vascular intima and of particles thus being released into the blood stream. The released particles can cause a vascular occlusion in blood vessels situated downstream.

Other known vascular supports comprise a flexible film that completely spans the lattice structure. In the treatment of stenoses composed of vulnerable plaque, the film prevents detached particles from moving into the blood stream and being swept away. Stenoses often occur in the area of vascular ramifications, for example in the area of the opening of the vertebral artery into the basilar artery or at the division of the common carotid artery into the internal carotid artery and the external carotid artery. The use of vascular supports with a closed film is not possible in areas such as these, since the flow of blood into the branching-off blood vessel would be interrupted. By contrast, vascular supports without a film have the aforementioned disadvantages in terms of the release of particles.

The use of film-covered vascular supports for treatment of aneurysms has basically the same disadvantages as have been described above in respect of the known flow diverters which have a relatively small mesh size. In the known flow diverters, and also in film-covered vascular supports, it is not possible to guide a catheter for introducing coils into the aneurysm.

It is an object of the invention to make available a medical device which, on the one hand, permits reliable support of a body cavity and, on the other hand, permits a lateral flow of fluid. In particular, it is an object of the invention to make available a medical device with which a flow of fluid within a body cavity can be chronologically controlled in a targeted manner. The invention is preferably intended to provide a medical device which reliably covers a stenosis and/or an aneurysm, and which at the same time permits a lateral flow of fluid in the area or vicinity of the stenosis and/or the aneurysm.

It is a further object of the invention to make available a medical device which prevents an axial flow of fluid counter to the main direction of flow of the fluid guided within the body cavity, and which permits a flow of fluid in the main direction of flow of the body fluid.

According to the invention, these objects are achieved, in terms of the lateral flow of fluid, by the subject matter of claim 1 and, in terms of the axial flow of fluid, by the subject matter of claim 2.

The invention is based on the concept of making available a medical device with a tubular wall made of webs, which delimit cells, and with a flexible membrane, which forms at least one flap. The flap has a first end connected to at least one first web of a cell. Moreover, the flap has a free second end arranged opposite the first end in the longitudinal direction of the flap. The flap is movable to a closed position and to an open position. In the closed position, the flap extends along the tubular wall and at least partially closes the cell. In the open position, the flap is radially deflected relative to the wall in order to free the cell in the manner of a valve.

The invention is based on the idea of covering the cells of the tubular wall with a flexible membrane that is designed like a flap. The flap-like membrane or the flap is radially deflectable in order to cover the cell in the closed position and to free the cell opening in the open position. The flap thus has a valve function. The flap can assume its closed position and its open position automatically, for example as a result of a pressure gradient, or generally a flow of fluid, which is formed between an inner hollow channel, extending axially inside the tubular wall, and an outer space, extending outside, in particular radially outside, the tubular wall. It is also possible that the closed position or open position of the flap can be adopted by manual actuation. For example, the flap can be opened by an external force, preferably by the advancing force of a catheter. Overall, the flap permits a reliable coverage of the cell in the closed position, for example in order to block a flow of blood into an aneurysm. At the same time, the flap is movable to the open position, such that, for example, coils can be introduced into an aneurysm. As soon as the aneurysm has been filled with a sufficient number of coils and the delivery catheter has been withdrawn, the flap closes the cell or cell opening automatically. This additionally prevents coils from passing from the aneurysm into the blood stream.

Provision is generally made that the flap, in the closed position, lies completely on the tubular wall 10. The flap thus extends substantially parallel along the tubular wall, specifically in substantially complete contact with the tubular wall. Alternatively, in the context of the application, the flap can also be arranged in the closed position, or assume the closed position, when the flap is slightly deflected relative to the tubular wall. This applies in particular in the manufactured state or rest state of the medical device. In the manufactured state of the medical device, the flap can thus be slightly deflected radially outward or radially inward, with significant opening of the cell advantageously being avoided. This basic deflection in the closed position can be conferred on the flap by heat treatment, for example. The basic deflection can be adapted such that the flap in the implanted state, for example through contact with a vessel wall, can be arranged lying parallel and flush on the tubular wall. The flush contact of the flap on the tubular wall in the implanted state can also be achieved through the influence of a flow of fluid that acts on the flap. Generally, the deflection for producing the open position of the flap is much greater than the basic deflection in the closed position of the flap. The valve function of the flap comes to bear when the flap is moved from the closed position to the open position and vice versa.

With the medical device according to the invention, aneurysms in particular can be reliably covered, while the introduction of coils into the aneurysm is permitted at the same time. By virtue of the flaps that cover the cells, the chosen distances between the webs of the tubular wall, i.e. the cell size, can be comparatively large in order to guide a catheter through the tubular wall. This has the advantage that the medical device has an improved crimping ability, i.e. a relatively small cross-sectional diameter in the compressed state, since the number of webs in the circumferential direction of the tubular wall is reduced. At the same time, the flexibility of the device is increased by the smaller number of webs.

The medical device according to the invention is particularly advantageous in aneurysms in the area of vascular ramifications. The flexible flap in this case permits a reliable coverage of the aneurysms, resulting in advantageous embolization within the aneurysm, such that the blood flow, and therefore the loads on the vessel wall, are reduced within the aneurysm. At the same time, the flap or a further flap is movable from the closed position to the open position by the blood stream which flows, in the area of the vascular ramification, into the lateral vessel in which the aneurysm is formed, such that a natural flow passage forms in which the blood, or generally the body fluid, can flow past the aneurysm into the lateral vessel.

The flap is connected at one end, namely at the first end, to a web of the tubular wall. The second end is free or arranged loosely. The second end lies opposite the first end in the longitudinal direction of the flap. The free second end is therefore movable in relation to the first end. With suitable positioning of the medical device in the area of a vascular ramification, this allows the flow of fluid within the hollow vessel to be influenced in a targeted manner. In the open position, the flap is deflected relative to the tubular wall, such that not only is the flow of fluid through the cell released, the released flow of fluid can also be influenced in terms of the direction of flow.

A further advantage of the medical device according to the invention is that the flexible membrane, which forms the at least one flap, ensures that particles transported with the flow of fluid can be conveyed in a preferred direction. For example, in the area of vascular ramifications, the flexible flap can ensure that fluid flows into a laterally branching-off vessel. At the same time, the flexible flap can prevent the particles, for example thrombus components, from flowing into the lateral vessel. In this way, the particles can be guided into regions of the body where a vascular occlusion causes relatively minor health problems.

According to an additional aspect, the invention is based on the concept of making available a medical device, in particular a stent, with a tubular wall, which forms an axial hollow channel and has webs that delimit cells. At least two flexible membranes are provided, which are arranged spaced apart from each other in the longitudinal direction of the axial hollow channel. The flexible membranes each form at least one flap. The flap has a first end connected to at least one first web of a cell. Moreover, the flap has a free second end arranged opposite the first end in the longitudinal direction of the flap. The flap is movable to an open position and to a closed position. In the open position, the flap extends along the tubular wall. In the closed position, the flap is radially deflected relative to the wall and protrudes into the axial hollow channel in order to at least partially close the axial hollow channel in the manner of a valve.

In accordance with the additional aspect of the invention and in contrast to the medical device that has been described above, the axial channel is to be closed temporarily by at least two flaps spaced apart axially from each other. For this purpose, the flap is firmly connected at a first end to a web of the tubular wall. The free second end is movable relative to the first end, in particular radially deflectable relative to the tubular wall. In the closed position, the flap closes the axial hollow channel. The medical device in accordance with the additional aspect of the invention has the advantage that the at least two flaps, which are spaced axially apart from each other and in the closed position at least partially close the axial hollow channel, simulate the function of venous valves. The flaps are therefore preferably adapted such that the flaps are movable from the closed position to the open position in each case as a result of a flow of fluid through the axial hollow channel. Preferably, the flaps are oriented and adapted in such a way that a flow of fluid in a first axial direction moves the flap from the closed position to the open position. A flow of fluid in a second axial direction counter to the first axial direction advantageously causes the flap to move from the open position to the closed position. The flaps therefore allow the flow of fluid through the axial channel to be influenced in such a way that the flow of fluid is possible in a single direction. A flow of fluid in the opposite direction is blocked. Alternatively, moving the flaps from the closed position to the open position can also be done manually.

By means of the two membranes spaced apart in the axial direction, the medical device can be used as a venous valve prosthesis with which at least two venous valves can be replaced at the same time. Alternatively, the medical device can also be used as a full vascular replacement or full vascular prosthesis. For example, the flaps can be arranged on an inner circumference of the tubular wall, and the outer circumference of the tubular wall can be enclosed by a film known per se, such that a tube-shaped vascular prosthesis is formed with a support structure of webs and with flaps closing an axial hollow channel.

In the device in accordance with the additional aspect of the invention, the flap in the open position can partially protrude radially into the hollow channel. This ensures that the flap automatically assumes the closed position when a flow of fluid counter to the first axial direction acts on the membrane.

The following preferred embodiments, including their effects and advantages, relate where appropriate to both of the claimed medical devices independently of each other.

In a first preferred embodiment, the cell has at least one first node point, which connects the first web to a second web. The first web and the second web enclose an angle in the area of the node point. The first end of the flap is connected to the first web and/or the second web in the vicinity, in particular in the area, of the first node point. Arranging the first end of the flap in the area or in the vicinity of a first node point has the effect of ensuring a sufficient coverage of the cell in an expanded state of the tubular wall. At the same time, excessive extension of the flexible membrane, in particular of the flap, is avoided during the transfer from the compressed state of the tubular wall to the expanded state.

The first end of the flap can be arranged on an outer circumference or an inner circumference of the tubular wall. The membrane overall can be arranged on the outer circumference or the inner circumference of the tubular wall. The arrangement of the membrane, or of the first end of the flap, on the outer circumference of the tubular wall has the advantage that a relatively uniform, smooth and planar outer skin is formed on the outer circumference. A configuration of this kind is advantageous, for example, for treatment of stenoses, in particular with vulnerable plaques, since the smooth outer skin avoids damage to the vulnerable plaque. An advantage of arranging the flexible membrane or the first end of the flap on the inner circumference of the tubular wall is the improved adhesion or fixing of the medical device in a hollow vessel of the body. In this configuration, the webs formed on the outer circumference of the tubular wall form a lattice structure which presses itself easily into preferably healthy vessel walls and thus fixes the medical device. On the inner circumference of the tubular wall, the flexible membrane, at least in the closed position of the flaps, forms a uniform inner skin, such that a hollow channel permitting optimized flow is formed. The comparatively smooth and uniform inner skin avoids thrombogenesis in the area of the medical device and therefore avoids restenosis.

In another preferred embodiment, the flap can be substantially leaf-shaped. Such a shape permits a reliable coverage of the cells or of the axial hollow channel. The leaf shape permits a particularly advantageous folding of the flap during the transfer of the tubular wall, or generally the medical device, from the expanded state to the compressed state. The leaf shape of the flap thus ensures that the tubular wall can be compressed to a relatively small cross-sectional diameter.

The flap preferably has a structuring, in particular a pore structure or a fluted structure or a fleece structure. The structuring of the flap permits endothelialization. This means that the structuring of the flap allows endothelial cells to settle. Rapid settling of endothelial cells is desirable, since in this way the risk of thrombosis or restenosis is reduced. The structuring can also have the effect that smaller tributary vessels can also be exposed to a flow of fluid, in which case the flow of fluid is made possible through the structuring of the flap. This is particularly advantageous if the cross-sectional diameter of the tributary vessel is smaller than the length or circumference of the flap. In addition, the structuring increases the flexibility of the flap or counteracts material stresses in the flap, which are triggered, for example, by stretching of the flap.

According to a preferred embodiment, the flap has a fold line, which extends at least in parts from the first end to the free second end. The fold line defines a preferred fold. The fold line preferably runs in the longitudinal direction of the flap. It is particularly advantageous if the fold line is flush with two node points arranged adjacent in the longitudinal direction of the tubular wall. This has the effect that the flap folds preferably radially through the cell when the medical device is transferred from the expanded state to the compressed state. In this way, a particularly small compressed shape of the medical device is possible. The fold line can divide the flap into a first flap wing and a second flap wing. Preferably, the first flap wing is connected to the first web of the cell, and the second flap wing is connected to the second web of the cell. This ensures that the flap folds uniformly along the fold line.

The fold line can comprise a groove and/or a gap, such that the folding of the flaps during the transfer of the medical device from the expanded state to the compressed state is made easier. According to a preferred embodiment, the gap can separate the first flap wing at least in parts from the second flap wing. The first flap wing can be connected to or formed in one piece with the second flap wing, in which case a portion that comprises the gap is provided between the first flap wing and the second flap wing. In the area of the gap, the first flap wing and the second flap wing are arranged spaced apart from each other. The gap is preferably arranged in the longitudinal direction of the flap. The gap can be open in the direction of the first node point, in the vicinity of which the first flap wing is connected to a first web and the second flap wing to a second web. The gap can separate the first flap wing completely from the second flap wing in such a way that the first flap wing is spaced apart completely from the second flap wing. In this case, the flap forms two individual flap parts, namely the first flap wing and the second flap wing. This further improves the folding or arranging of the flap in the compressed state of the medical device. Moreover, the division of the flap into two separate flap wings makes the transfer from the closed position to the open position easier. The valve function can thus be improved overall.

As has been explained above as an advantage, the flap is movable automatically from the closed position to the open position.

In a preferred embodiment, the free end of the flap can protrude, in the closed position, into the cell, in particular can be arranged inside the cell, or can overlap the cell. The overlapping of the cell takes place at least in the longitudinal direction of the medical device. This means that, in the circumferential direction of the tubular wall, partial areas of the cell may not be covered by the flap. When the flap overlaps the cell, the free end of the flap extends past the cell in the longitudinal direction or axial direction of the tubular wall.

The overlapping ensures that, in the expanded state of the tubular wall or generally of the medical device, the cell is reliably covered when the flap has assumed the closed position. Alternatively, in the closed position of the flap, the cell may be partially uncovered in the expanded state of the tubular wall or of the medical device.

It is possible that the flap, in the closed position, extends in the longitudinal direction or in the circumferential direction of the tubular wall. The extending of the flap, in the closed position, in the longitudinal direction or axial direction of the tubular wall is particularly preferred.

In a preferred embodiment of the medical device, the membrane has several flaps. The several flaps, in the closed position, extend along the tubular wall. In each case, a free end of a first flap overlaps, in the manner of a roof tile, at least one first end, particularly two first ends, of an adjacent flap. The overlapping of the flaps in the manner of roof tiles is discernible at least in a compressed state of the tubular wall or generally of the medical device. Preferably, the overlapping in the manner of roof tiles is also provided in the expanded state of the tubular wall. The overlapping in the manner of roof tiles can be provided at least in the circumferential direction in the compressed state of the tubular wall. In the overlapping in the manner of roof tiles, at least one first flap overlaps at least one second flap, preferably two second flaps. The first flap can extend in the longitudinal direction of the tubular wall, in which case the second free end extends substantially between two second flaps arranged spaced apart in the longitudinal direction of the tubular wall.

In other words, the medical device according to this illustrative embodiment comprises several rows of flaps arranged adjacent in the axial direction of the tubular wall, in which case the flaps of rows immediately adjacent in the axial direction are arranged offset in relation to one another. Thus, the first flaps of a first row overlap two second flaps of a second row. In particular, in the compressed state of the tubular wall, the second free ends of the first flaps of a first row overlap two first, fixed ends of two second flaps of a second row. It is also possible that the second free ends of the first flaps of a first row overlap two second free ends of two second flaps of a second row. In other words, the flaps of adjacent rows can be arranged in opposite directions. The same applies analogously to an arrangement of the flaps in the circumferential direction of the tubular wall. The first row and the second row of flaps in this case extend in the longitudinal direction. The first flaps of the first row overlap at least one second flap, in particular two second flaps, of a second row of flaps arranged adjacent in the circumferential direction. In the expanded state of the tubular wall, the first flaps of the first row can partially overlap at least the cells of the second row. In this case, the first flaps of the first row can extend between two second flaps of the second row.

According to a preferred embodiment of the medical device in accordance with the additional aspect of the invention, the at least two membranes each form a multiple flap. The multiple flap is movable from a closed position to an open position. Preferably, the multiple flap has at least two flaps which are arranged radially opposite in relation to a longitudinal axis of the axial hollow space. In the closed position, the at least two flaps extend into the axial hollow space in order to close the axial hollow space in the manner of a valve. The multiple valve is particularly advantageous in respect of fluid dynamics.

The free second ends of the flaps of the multiple flap can touch in the closed position. This ensures that the axial hollow space is safely closed. In the closed position of the multiple flap, or generally of the flap, the axial hollow space is preferably closed in a fluid-tight manner.

A cell preferably has two flaps which, in an expanded state of the cell, are arranged opposite each other and, in a compressed state of the cell, are arranged laterally alongside each other. In relation to the individual cell, this arrangement has the advantage that a large area of the cell is covered, without the cell being too long. In relation to a cell with more than two flaps, in particular with 4 flaps, the advantage of this is that crimping is made easier, since the cover or flaps overlap the structure and not one another during the crimping.

In another embodiment, at least in the area of the first end of the flap, a pore structure, in particular a perforation of the flap, is formed which extends into the area of the first web, wherein the first end is connected in parts to the first web in such a way that the pore structure of the first end is deformable in the loose area or in the loose areas. In this way, a deformation of the cover or of the flap is avoided or at least reduced.

It will be noted that the above-described advantageous embodiments of the invention generally describe the expanded state of the medical device, unless explicitly stated otherwise. This also applies to the following description of preferred illustrative embodiments.

The invention is explained in more detail below on the basis of illustrative embodiments and with reference to the attached schematic drawings, in which:

FIGS. 1 and 2 each show a plan view of a tubular wall of a medical device according to the invention, in each case according to a preferred illustrative embodiment;

FIGS. 3 to 9 each show a longitudinal section through a medical device according to the invention, in each case according to a preferred illustrative embodiment and in different positions of insertion;

FIGS. 10 to 14 each show a detailed view of a flap of a medical device according to the invention, in each case according to a preferred illustrative embodiment;

FIG. 15 shows a plan view of a tubular wall of a medical device according to the invention, in another preferred illustrative embodiment;

FIGS. 16a and 16b each show a cross section through a medical device in accordance with the additional aspect of the invention and according to a preferred illustrative embodiment, with different positions of the flaps;

FIGS. 17a to 17c each show a cross-sectional view through a tubular wall with a flap according to a preferred illustrative embodiment;

Figure 1:
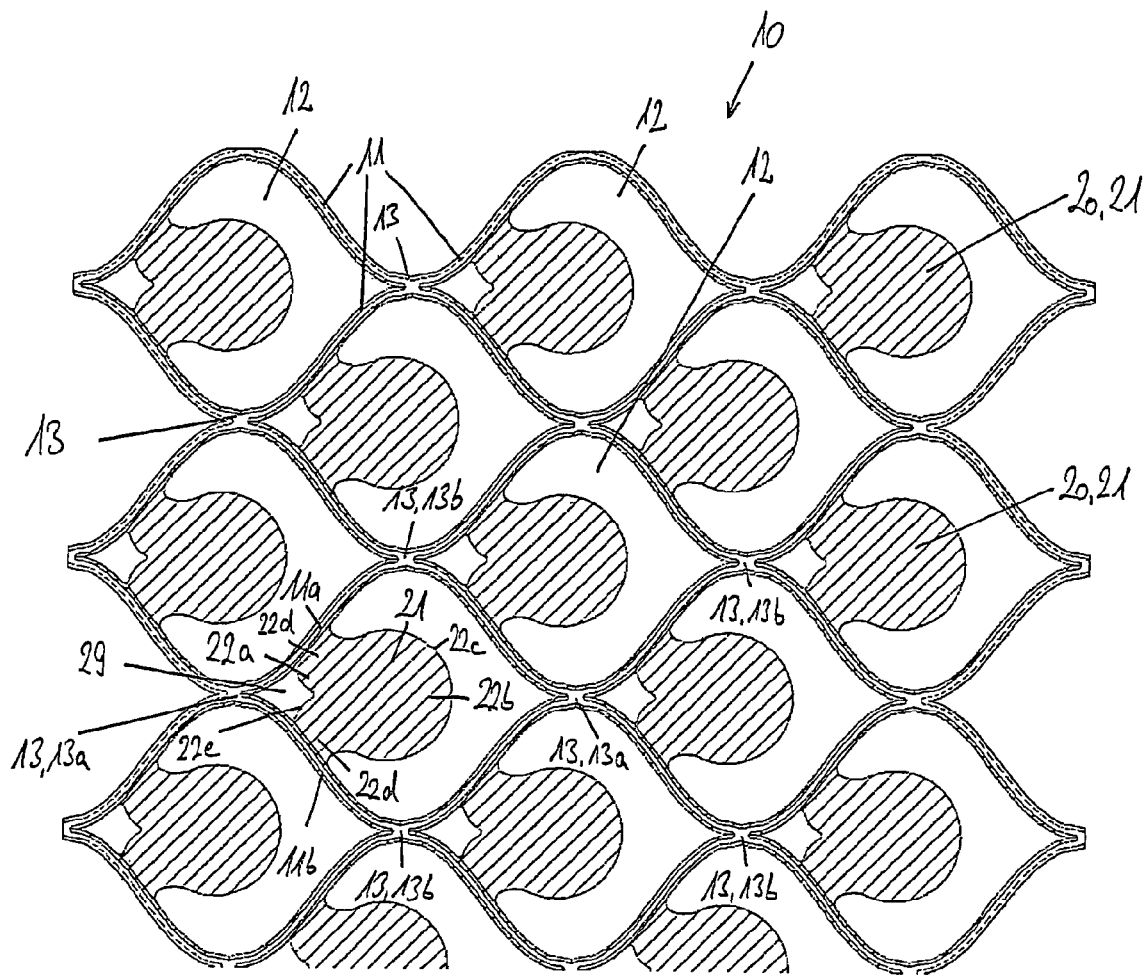

FIG. 1 shows the expanded state of a tubular wall 10 or generally of the medical device. The same applies to all the illustrative embodiments shown in FIGS. 1 to 17c. For reasons of clarity, FIG. 1 shows the tubular wall 10, or the cutout of the tubular wall 10, in the state when folded open and spread flat out. The axial longitudinal axis of the tubular wall 10 extends substantially horizontally in the drawing plane in FIGS. 1, 2, 3, 7 and 10 to 15.

The detailed cutout of the wall 10 in FIG. 1 shows several webs 11, which in each case connect two node points 13 to each other. In the expanded state, the webs 11 are S-shaped. Four webs 11 are in each case connected to one another at a node point 13. Four webs 11 in each case delimit a cell 12 of the tubular wall 10. The cells 12 are completely delimited by webs 11. The tubular wall 10 according to FIG. 1 thus forms a closed-cell structure. It is alternatively possible that the tubular wall 10 has an open-cell structure, in which case at least two webs 11 are freely movable, i.e. not connected to each other, at a node point 13. In this case, the webs 11 can instead form end arches which, during the transfer of the tubular wall, or generally of a lattice structure formed by the webs 11, from the compressed state to the expanded state, can change their position relative to the lattice structure. For the illustrative embodiments described in the context of this application, the closed-cell structure is preferred.

The webs 11 as a whole form the lattice structure or the tubular wall 10. In other words, the medical device has a support structure formed by the webs 11 connected at the node points 13.

The cells 12 each comprise a first web 11a and a second web 11b, wherein the first web 11a and second web 11b are connected to each other at a first node point 13a. The first web 11a and the second web 11b extend from the first node point 13a to a second node point 13b, wherein the node points 13a and 13b are adjacent in the longitudinal direction of the tubular wall 10 and are offset in the circumferential direction. This applies in particular in the expanded state of the tubular wall 10. Starting from the first node point 13a, the first web 11a and the second web 11b enclose an angle. The first node points 13a of adjacent cells 12 are aligned with one another. This applies both for the longitudinal direction of the tubular wall 10 and also for the circumferential direction. The same applies to the second node points 13b of adjacent cells 12.

The tubular wall 10 also has a flexible membrane 20. The flexible membrane forms at least one flap 21. According to the illustrative embodiment in FIG. 1, several flaps 21 are provided, wherein one flap 21 is in each case assigned to a single cell 12. The flap 21 comprises a first end 22a, which is connected to the first web 11a and to the second web 11b. The first end 22a is preferably integrally bonded to the first web 11a. The connection to the second web 11b is preferably also effected by integral bonding. The first end 22a of the flap 21 is arranged in the vicinity of a node point 13, in particular of the node point 13a.

It will be noted in this context that all points of the web 11 that are at a distance from the node point 13 equal to at most half the length of the web 11 are regarded as points or areas located in the vicinity of the node point 13. Here, the distance refers to the path between the point in question and the node point 13 along the web 11. In other words, the half of the web 11 directed toward the node point 13, or connected to another web 11 at the node point 13, belongs to the vicinity of this node point 13.

The flap 21 also has a free second end 22b, which is arranged opposite the first end 22a in the longitudinal direction of the flap 21. In the illustrative embodiment according to FIG. 1, the flap 21 extends in the longitudinal direction of the tubular wall 10. The first end 22a and the second end 22b of the flap 21 are arranged in succession in the longitudinal direction of the flap 21 or of the tubular wall 10. The flap 21 as a whole is aligned with the first node points 13a of adjacent cells 12 arranged in succession in the longitudinal direction of the wall 10.

As is also shown in FIG. 1, the flap 21 is substantially leaf-shaped. The second free end 22b in particular forms a curved free edge 22c of the flap 21. The free edge 22c extends over the free second end 22b and is delimited by the first and second webs 11a, 11b. The shape of the free edge 22c between the first web 11a and the second web 11b corresponds substantially to an omega. The first end 22a comprises two holding portions 22d, which are each connected to the first web 11a or the second web 11b. Between the holding portions 22d, an inner edge 22e is formed in the area of the first end 22a. The inner edge 22e extends along the holding portions 22d from the first web 11a to the second web 11b. The inner edge 22e has an opposite curvature in the two holding portions 22d. The inner edge 22e thus forms a tent-shaped indent in the flap 21. Together with the first web 11a and the second web 11b, the inner edge 22e encloses a fold opening 29. The fold opening 29 is substantially kite-shaped or deltoid with inwardly curved side edges. The longer diagonal of the kite extends in the longitudinal direction of the flap 21 or of the tubular wall 10.

In the illustrative embodiment according to FIG. 1, the flap 21, in the closed position, extends into the cell 12. This means that the flap 21 partially covers the cell 12 in the closed position. It can be clearly seen in FIG. 1 that the flap 21 covers a central area of the cell 12. An outer area of the cell 12, formed between the webs 11 and the free edge 22c, is uncovered and permeable to fluid. It is also possible for the flap 21 to be shaped in such a way that the cell 12 is completely covered in the closed position of the flap 21 and in the expanded state of the tubular wall 10. For example, the fold opening 29 can also be covered by the membrane 20 or the flap 21.

Figure 2:
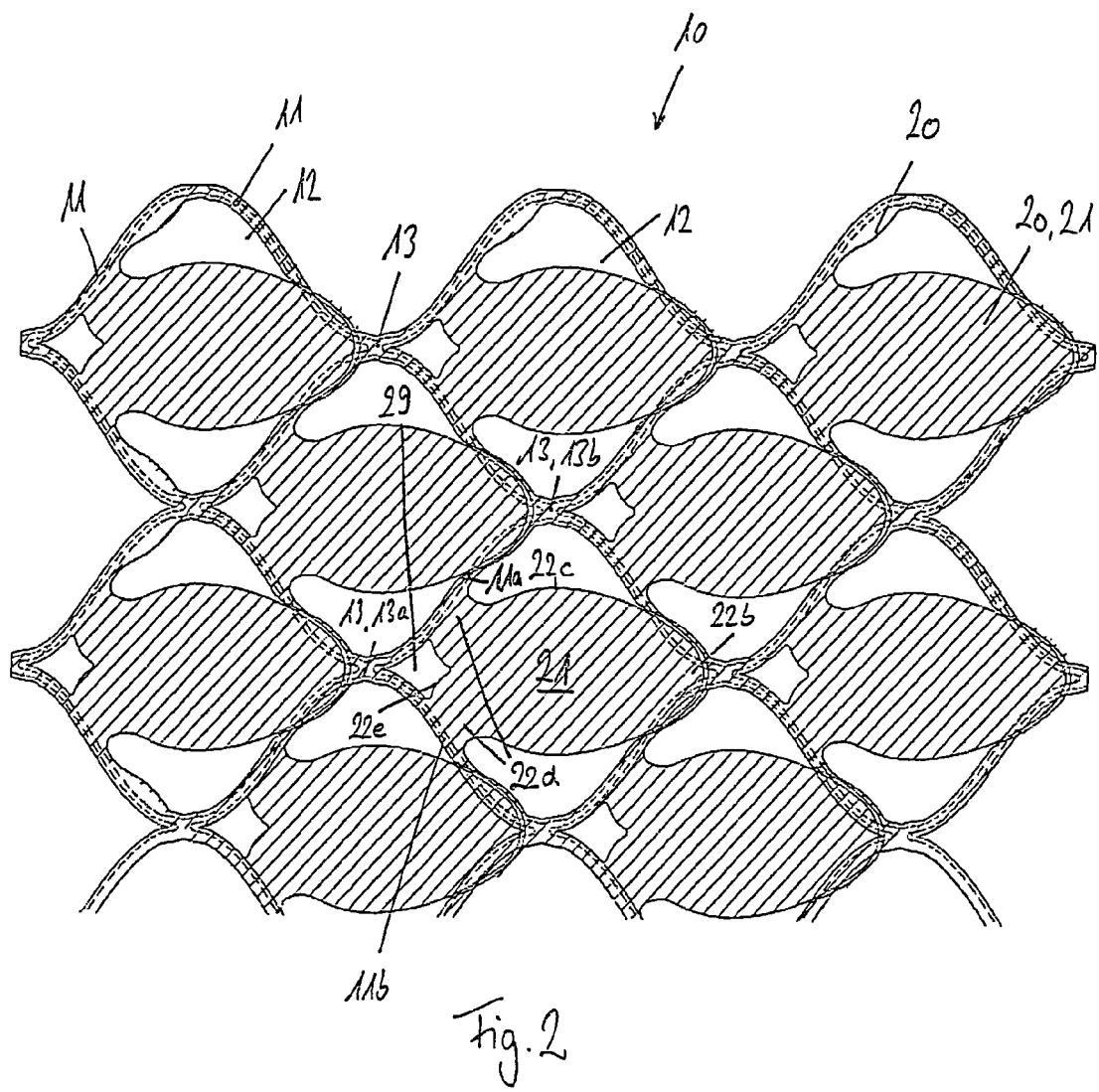

Another illustrative embodiment of the medical device, in which the flap 21 covers a larger area of the cell 12, is shown in FIG. 2. The illustrative embodiment according to FIG. 2 corresponds substantially to the illustrative embodiment according to FIG. 1, the flap 21 having a comparatively greater length and overlapping the cell 12. This means that, in the closed position, the second free end 22b of the flap 21 is arranged lying on the webs 11 in the area of the node point 13, particularly of the node point 13a of an adjacent cell 12. The flap 21 thus overlaps the cell 12. In the illustrative embodiment according to FIG. 2, provision is also made to stretch the membrane 20 onto areas of the first web 11a and of the second web 11b that are arranged at a distance from the first node point 13a. The membrane 20 thus forms a wing-like widening along the web 11. The wing-like widening itself is described in detail in the German Patent no. 10 2008 010 507, which was filed by the applicant. A combination of the medical device with the wing-like widenings of the webs 11 described therein is hereby explicitly disclosed.

The membrane 20 can be arranged on the outer circumference 14a of the tubular wall 10. The flaps 21 in this case extend over the outer circumference 14a. Alternatively, the membrane 20 can be arranged on an inner circumference 14d of the tubular wall 10. In this case, the flaps 21 extend along the inner circumference 14b. In both cases, the flaps 21 can extend in the longitudinal direction of the wall 10. It is also possible that the flaps 21 extend in the circumferential direction of the wall 10. Moreover, the flaps 21 can each extend in the same direction. This means that, in the closed position, in each case a free second end 22b of a first flap 21a is flush with and overlaps a fixed first end 22a of a second flap 21b. Alternatively, the flaps 21 of adjacent cells 12 can be arranged in opposite directions. For example, a first flap 21a and a second flap 21b, adjacent in the longitudinal direction of the first flap 21a, can each have a free second end 22b, in which case the free second ends 22b are arranged adjacent to each other or overlapping each other.

Generally, the flaps 21 or the membrane 20 are flexible. In particular, the flaps 21 are flexible in such a way that the second free end 22b of the flap 21 is radially deflectable relative to the first fixed end 22a. The flap 21a is therefore flexible in such a way that the flap 21a is movable to an open position, in which the flap 21 does not cover the cell 12. The cell 12 is substantially freely permeable in the open position of the flap 21. The flap 21, in particular the second free end 22b, is deflected in the open position or bent radially with respect to the tubular wall 10. The flap 21 can be curved both to the outside and also to the inside. In the open position, the free end 22b thus points either radially outward or radially inward relative to the tubular wall 10. It is unimportant here whether the flap 21 is arranged with the first end 22a on the outer circumference 14a or on the inner circumference 14b of the tubular wall. The flap 21 is preferably adapted such that a radially outward deflection takes place when the first end 22a of the flap 21 is connected to the outer circumference 14a of the tubular wall 10. Analogously, the flap 21 is preferably adapted such that a radially inward deflection takes place relative to the tubular wall 10 when the flap 21 is arranged with the first end 22a on the inner circumference of the tubular wall 10.

In general, the medical device comprises two main functional elements. On the one hand, a supporting structure is provided, particularly in the form of the tubular wall 10 which preferably comprises a lattice structure of webs 11 and which ensures the stability or strength in the radial direction. The supporting structure can have substantially a stent-like geometry. On the other hand, the medical device has a cover, particularly in the form of the membrane 20, which forms flaps 21. The flaps 21 protrude into the cells 12 and/or overlap them. In the closed position, the cell 12 is at least partially covered, in particular completely covered, by the flap 21. The flexible flap 21 has a valve function. For this purpose, the flap has the first fixed end 22a and the second free or loose end 22b.

Particularly advantageous design features of the membrane 20 are explained below:

The function of the membrane 20 or of the flap 21 is in particular to free the cell 12 in the manner of a valve. This can be done in particular by means of a pressure gradient that forms between the sides of the cell, particularly an inner axial hollow channel 30 of the tubular wall 10 or of the medical device, and an area radially outside the tubular wall 10. In general, it is advantageous if the flexible flap 21 is movable to the open position or closed position by means of a flow of fluid acting on the flap 21. A high degree of flexibility of the flap 21 is advantageous. The flap 21 can be designed substantially as a film. The wall thickness of the flap 21 can be comparatively small. The comparatively small wall thickness not only improves or facilitates the valve function but also improves the crimping of the tubular wall 10, since the relatively thin flap 21 folds itself into the cell 12, and the thin wall thickness ensures that a relatively small crimped cross-sectional diameter is achievable for the tubular wall 10. In order to achieve this, provision is advantageously made that the membrane 20, in particular the flap 21, has a wall thickness of at most 15 µm, in particular at most 10 µm, in particular at most 8 µm, in particular at most 6 µm, in particular at most 4 µm, in particular at most 2 µm, in particular at most 3 µm, in particular at most 2 µm.

The relatively small wall thickness of the flap 21 also ensures that the flap 21 flutters when a body fluid, in particular blood, flows through the cell 12. Turbulent flow conditions can thus advantageously form in the area of the flap 21, such that, for example, a build-up of blood is avoided, or blood coagulation, in particular thrombogenesis, is counteracted. Instead, the fluttering movement of the flap 21 ensures a constant, continuous through-flow in the open position.

The flap 21 preferably extends to cover the entire cell 12. The flap 21 covers at least 10%, in particular at least 20%, in particular at least 30%, in particular at least 40%, in particular at least 50%, in particular at least 60%, in particular at least 70%, in particular at least 80% of the cell 12 in the expanded state. The greatest possible circular diameter discernible in an area left free by the flap 21 is at most 80%, in particular at most 60%, in particular at most 40%, in particular at most 30%, in particular at most 20%, in particular at most 10% of the size of the cell 12, wherein the size of the cell 12 corresponds to the diameter of the largest possible circle that can be arranged in the cell 12.

The flap 21 can also have a structuring, in particular a surface structuring, which, for example, promotes the endothelialization of the medical device. For example, the structuring can comprise a pore structure 28. The structuring can have a plurality of openings, which are introduced into the flap 21 and which pass completely through the flap 21 in the radial direction relative to the lattice structure 10.

In general, the distance between two node points arranged adjacent in the longitudinal direction of the medical device changes when the state of the wall 10 changes, i.e. when the wall 10 moves from the radially compressed state to the radially expanded state, and vice versa. In particular, the transition from the radially expanded state to the radially compressed state of the wall 10 causes a lengthening of the distance between node points 13, 13a arranged adjacent in the longitudinal direction of the medical device. The S-shaped webs 11 are able to deform, which can lead to a stretching of the flap 21. The structuring, in particular the patterned pore structure 28, facilitates the stretching or expanding of the flap 21. In particular, the pore structure 28 avoids stresses occurring in the flap 21 or generally in the membrane 20.

Figure 14:
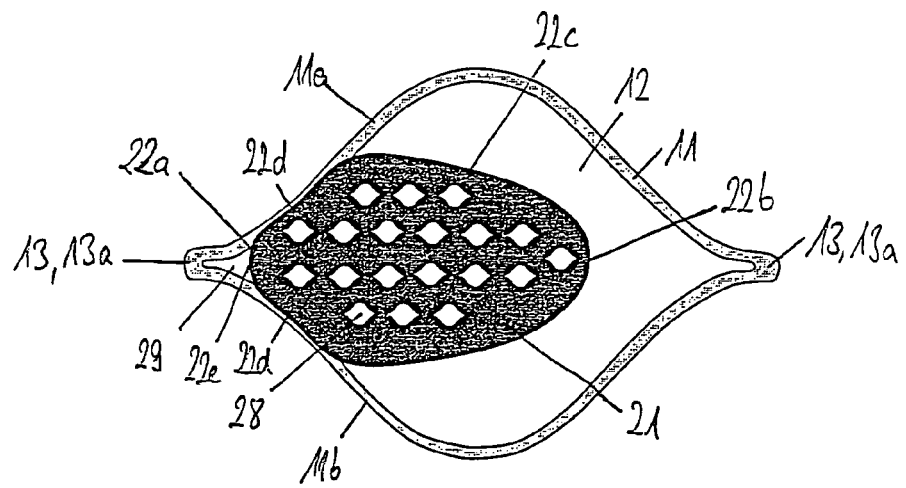
Figure 15:
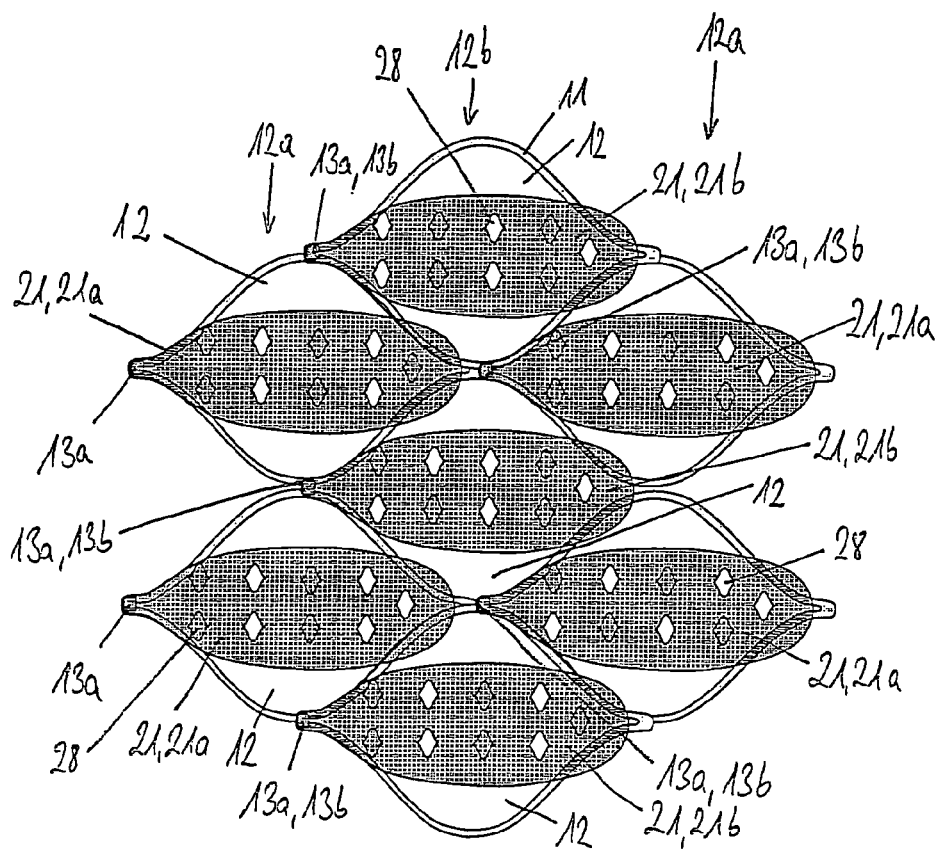

The pore structure 28 preferably has pores of diamond-shaped design. The diamond-shaped pores advantageously comprise two opposite corners that have a relatively large angle. For example, the angle can be at least 90°, in particular at least 120°, in particular at least 130°, in particular at least 140°, in particular at least 150°, in particular at least 160°, in particular at least 170°. The corners with the larger corner angle are preferably arranged lying opposite in the circumferential direction of the tubular wall 10. The pores of the pore structure 28 are preferably distributed in a pattern, i.e. regularly, over the flap 21, as is shown in FIGS. 14 and 15 for example.

The pores of the pore structure 28 can also be slit-shaped. The corner angles or the pores, arranged lying opposite in the circumferential direction of the tubular wall 10, are therefore almost 180° or exactly 180°. The gap width of the slit-shaped pores can be at most 300 µm, in particular at most 200 µm, in particular at most 100 µm, in particular at most 50 µm. In general, the relatively large angle of the opposite corners of the pores of the pore structure 28 results in a particularly high degree of flexibility of the flap 21 or generally of the membrane 20. A stretching of the membrane 20, or of the flap 21, is thus effectively avoided or at least reduced. The above-described pore structure 28 can be combined with all of the illustrative embodiments.

The flap 21 is generally flexible in such a way that, in the open position, a deflection is permitted which, in relation to the closed position, measures at least 20°, in particular at least 30°, in particular at least 45°, in particular at least 60°, in particular at least 90°. The deflection occurs in the elastically deformable area of the flap 21. Upon the deflection of the flap 21 in the open position, the flap 21 is curved. The maximum radius of curvature, or the radius of curvature at the most strongly curved area of the flap 21, is preferably at most 2 mm, in particular at most 1.5 mm, in particular at most 1 mm, in particular at most 0.8 mm, in particular at most 0.6 mm, in particular at most 0.4 mm, in particular at most 0.2 mm, in particular at most 0.1 mm, in particular at most 0.05 mm. Generally, the flap 21 is preferably flexible in such a way that it can be deflected to different extents depending on the physiological circumstances at the treatment site.

The flap 21 can have different geometries, as is explained below with reference to FIGS. 10 to 14:

FIGS. 10 to 14 each show a single cell 12 of a medical device according to a preferred illustrative embodiment. In general, the medical device can have at least one cell 12, which is designed with a flap 21 according to one of the illustrative embodiments in FIGS. 10 to 14. It is also possible that the medical device has several cells 12, which comprise differently shaped flaps 21. In other words, the medical device, or the wall 10, can have any desired combination of cells according to FIGS. 10 to 14. Preferably, the wall 10 has several cells of the same type. In particular, provision is made that the flaps 21 shown individually in FIGS. 10 to 14 are present multiply in a tubular wall 10 and interconnected. The mutually adjacent flaps 21, which are present multiply in the wall 10, are preferably interconnected in such a way that the flaps 21 together form a single membrane 20. Conversely, the wall 10 preferably has a single membrane, which forms several flaps 21. The flaps 21 can be arranged in directly adjacent cells 12. It is also possible that the flaps 21 are distributed across the wall 10 of the medical device in such a way that free cells 12 are arranged at least between individual flaps 21.

The membrane is connected to the support structure or the webs 11 substantially at points. The point connection between the membrane 20 and the webs 11 is preferably provided at those locations that in each case form the first end 22a of a flap 21. In relation to the webs 11, the connection of the membrane 20 is provided substantially in the vicinity of a node point 13. The membrane 20 or the flap 21 is preferably connected at those locations of the webs or of the wall 10 which, during the transition of the medical device from the compressed state to the expanded state, undergo a relatively small movement. Particularly preferably, the connection of the flap 21, in particular of the first end 22a, is directly in the node area 13, which does not substantially deform during the expansion of the medical device. The flap 21 is at least arranged between the first web 11a and the second web 11b in the vicinity of the node point 13. The first web 11a and the second web 11b enclose an acute angle. During the expansion of the tubular wall 10, a comparatively small relative movement takes place in the area of the acute angle between the first web 11a and the second web 11b. It is particularly preferable if the first end 22a of the flap 21, as is shown in FIGS. 10 to 14, is secured on an area of the webs 11 which is curved in the direction of the flap 21 or in the direction of the center of the cell 12. This has the effect of causing the flap 21 to fold during the compression or crimping of the medical device. Stretching, that is to say the generation of a stress within the flap 21, is thus avoided during the compression of the medical device.

Figure 10:
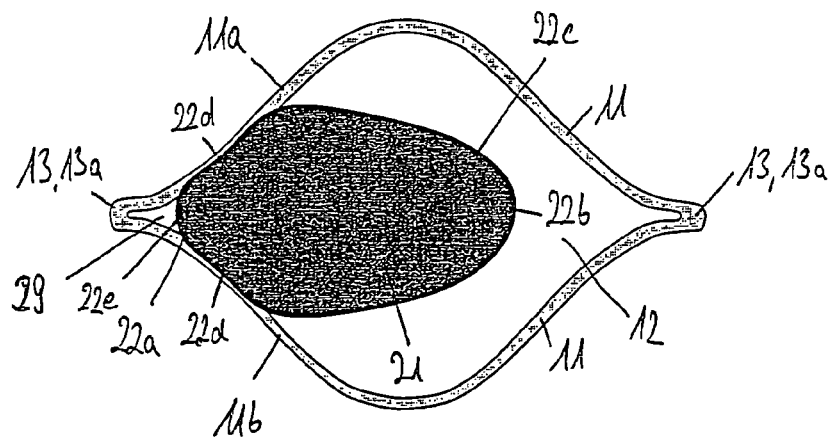
Figure 11:
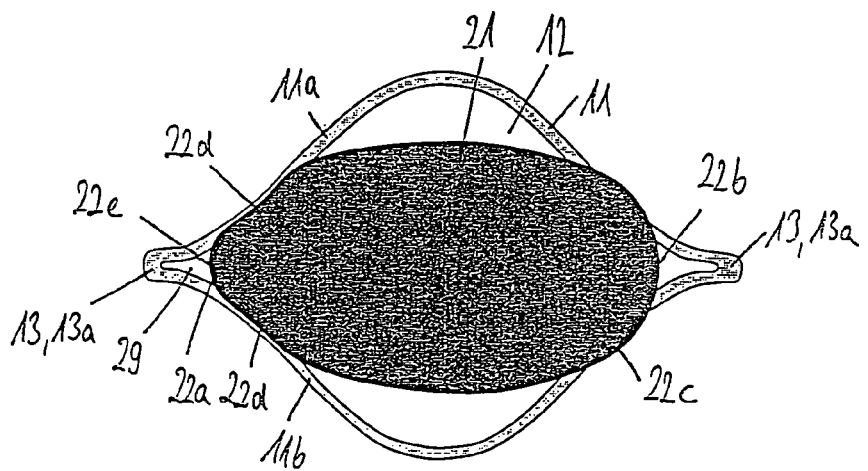

The geometry of the cell 12 and of the flap 21 according to FIGS. 10 and 11 corresponds substantially to the geometry of the cells 12 and of the flaps 21 according to FIGS. 1 and 2. A difference from the illustrative embodiments according to FIGS. 1 and 2 is that the leaf shape of the flap 21 comprises a flatter free edge 22c in the direction of the second end 22b. The free edge 22c according to FIG. 10 is substantially parabola-shaped. This means that the free edge 22c, starting from the first web 11a to the second web 11b, has substantially a uniform curvature in the clockwise direction, wherein the radius of curvature varies. The same applies basically to the illustrative embodiment according to FIG. 11, in which a front portion of the free edge 22c in the area of the second end 22b is flatter compared to the illustrative embodiment in FIG. 10. Moreover, the side portions of the free edges 22c, which extend between the second free end 22b of the flap 21 and the first and second webs 11a, 11b, are more strongly curved outward by comparison with the illustrative embodiment in FIG. 10. Overall, the illustrative embodiments according to FIGS. 10 and 11 differ from each other in that the flap 21 according to FIG. 10 extends into the cell, whereas the flap 21 according to FIG. 11 extends past the cell 12 or overlaps the cell 12. According to FIG. 10, the second end 22b of the flap 21 is arranged completely within the cell 12. It will be seen from FIG. 11 that the second end 22b of the flap 21 protrudes over the wider webs of the cell 12. In the closed position, the flap 21 lies loosely or freely, in particular without connection, on the wider webs 11.

In the illustrative embodiments according to FIGS. 10, 11 and 14, the inner edge 22e of the flap 21 has a curvature directed toward the first node point 13a. The curvature of the inner edge 22e extends from the first web 11a to the second web 11b uniformly or continuously in the counterclockwise direction. An indent into the flap 21 is not formed with the inner edge 22e according to FIGS. 10, 11 and 14. The fold opening 29, formed by the first web 11a, the second web 11b and the inner edge 22e of the flap 21, is substantially funnel-shaped.

Figure 12:
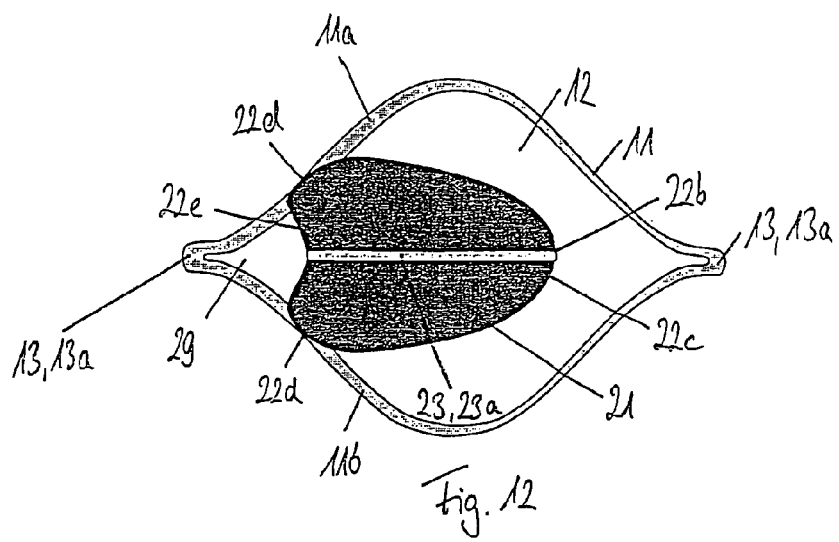

It will be seen from FIG. 12 that the flap 21 can have a fold line 23, which extends substantially in the longitudinal direction of the flap 21. The fold line 23 is aligned with two node points 13, which are arranged in succession and in alignment with each other in the longitudinal direction or axial direction of the tubular wall 10. In particular, the fold line 23 is in alignment with two first node points 13a of two cells 12 that are directly adjacent in the longitudinal direction of the wall 10. As in FIG. 12, the fold line 23 can comprise a groove 23a. The groove 23a is preferably adapted in such a way that a folding of the flap 21 is made easier during the compression of the tubular wall 10. In particular, the groove 23a provides a defined fold edge, which serves substantially as a rotation axis about which a first flap wing 24a and a second flap wing 24b of the flap 21 are rotatable for folding. The first flap wing 24a and the second flap wing 24b are therefore folded over each other along the fold line 23, in particular the groove 23a, during the compression of the tubular wall 10.

The groove 23a can be produced by an etching method for example. The groove 23a preferably has a depth that corresponds to at least 25%, in particular at least 30%, in particular at least 40%, in particular at least 50%, in particular at least 60%, in particular at least 70%, in particular at least 75% of the wall thickness of the flap 21. It is also possible to provide several grooves 23a, which extend in different orientations over the flap 21. In this way, the folding of the flap 21 can be permitted in complex geometries. The groove 23a extends in a straight line across the flap 21. The groove 23a can also extend in another orientation, in particular in an alternating orientation across the flap 21. During the compression of the tubular wall 10, the flap wings 24a, 24b advantageously fold radially inward, in order to make it easier to arrange the medical device in a catheter 60. It is also possible that the flap 21 has several fold lines 23, such that multiple folding is achieved. The multiple folding can be accordion-like. The fold lines 23 can also extend in part in the circumferential direction of the tubular wall 10. Generally, the fold lines 23 can extend in sections across the flap 21. The fold line 23 can also have a rib or a projection, which forms a rotation axis for the folding of the flap wings 24a, 24b.

FIG. 12 also shows another possible configuration of the fold opening 29. The fold opening 29 basically has a kite shape, wherein the shorter edges of the kite that are formed by the inner edge 22e have a curvature. This means that the corner formed by the two shorter edges of the kite, which corner is arranged at the intersection of the fold line 23 with the inner edge 22e, is rounded. In the expanded state of the tubular wall 10, the free second end 22b of the flap 21 according to FIG. 12 is arranged completely within the cell 12.

Figure 13A:
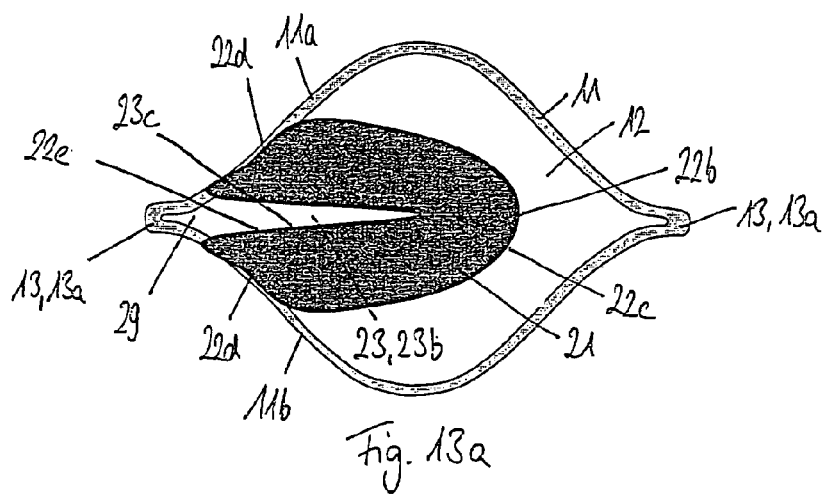
Figure 13B:
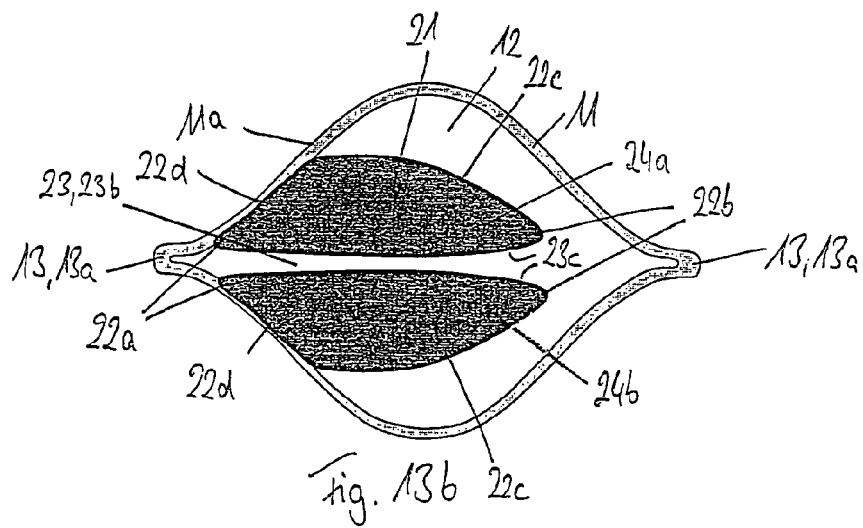

In the illustrative embodiments according to FIGS. 13a and 13b, the fold line 23 has a gap 23b, wherein the gap 23b according to FIG. 13a partially divides the flap 21. The gap 23b thus corresponds substantially to a pronounced form of the indent made in the other illustrative embodiments by the inner edge 22e of the flap 21. In particular, the inner edge 22e according to FIG. 13a has two straight gap edges 23c, which converge toward the center of the cell 12. In the expanded state of the tubular wall 10, the fold opening 29 is thus continued into the center of the cell 12. This has the effect that, during the expansion of the wall 10, the first flap wing 24a and the second flap wing 24b are movable relative to each other, such that stresses acting on the flap 21 during the expansion of the wall 10 are avoided. In particular, a stretching of the flap 21 in the circumferential direction of the tubular wall 10 is avoided.

As is shown in FIG. 13b, the gap 23b can completely divide the flap 21 into a first flap wing 24a and a second flap wing 24b. The cell 12 thus has two separate flap wings 24a, 24b, which are each connected to a single web 11. The free ends of the flap wings 24a, 24b protrude into the cell 12 in the expanded state of the tubular wall 10. It is also possible that the free ends of the flap wings 24a, 24b overlap the cell 12, that is to say protrude over the wider webs 11 in the expanded state of the wall 10.

Figure 18:
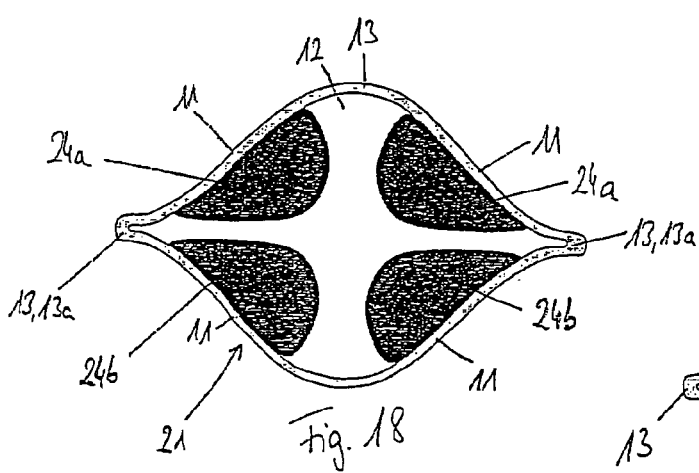
FIG. 18 shows a detailed view of a flap of a medical device according to the invention, in a preferred illustrative embodiment.

A similar illustrative embodiment is shown in FIG. 18, where a total of four flap wings 24a, 24b form a flap 21. The four flap wings are each arranged on a web 11 of the cell 12. The connection between the flap wings 24a, 24b and the webs 11 is preferably linear. This means that the flap wings 24a, 24b each have a connection line that extends along the associated web 11. It applies generally to all the illustrative embodiments that the flap 21 can be connected linearly to the web 11. Alternatively, in all the illustrative embodiments, provision can be made that the flap 21 is connected to the web 11 at points. Moreover, it generally applies that the flap 21 is preferably connected to a comparatively straight or rectilinear portion of the web 11. It is thus possible to avoid a situation where, during the compression of the tubular wall 10, forces act on the flap 21 and cause the flap 21 to fold or stretch. In the illustrative embodiment according to FIG. 18, for example, this is achieved by the fact that the flap wings 24a, 24b are each connected to a central area of the associated web 11. In particular, the connection between the flap wings 24a, 24b and the web 11 is provided in a comparatively rectilinear area in the middle of the S-shaped web 11. In the other illustrative embodiments according to FIGS. 10 to 14, the flap 21 is relieved, during the compression of the tubular wall 10, for example by the fact that either a fold opening 29 or a gap 23b is provided. In this way, a connection of the flap 21 or of the flap wings 24a, 24b is avoided in areas of the webs 11 which greatly deform during the transition of the tubular wall 10 from the compressed state to the expanded state, and vice versa.

Figure 19:
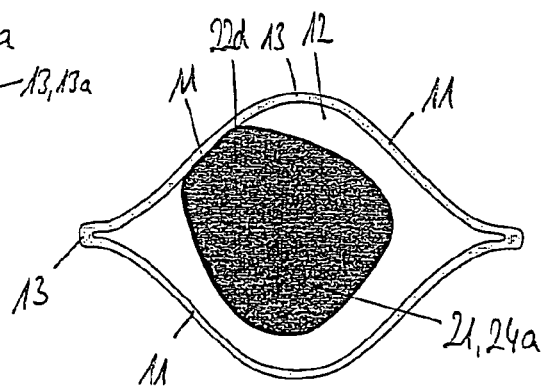
FIG. 19 shows a detailed view of a flap of a medical device according to the invention, in another preferred illustrative embodiment.

Another illustrative embodiment, in which the flap 21 is articulated on or connected to the web 11 in a rectilinear area of the web 11, is shown by way of example in FIG. 19. Here, the flap 21 is formed by a single flap wing 24a, which has a holding portion 22d connected linearly to the web 11, in particular to a rectilinear area of the web 11. Alternatively, a connection is also possible only at points. For all the illustrative embodiments in which the connection between the flap 21 and the web 11 is provided in a rectilinear area of the web 11, provision is advantageously made that the length of the rectilinear area of the web 11 in relation to the total length of the web 11, i.e. to the distance between two node points 13 connected by an S-shaped web 11, is at least 10%, in particular at least 20%, in particular at least 30%, in particular at least 40%, in particular at least 50%, in particular at least 60%, in particular at least 70%, in particular at least 80%, in particular at least 90% of the web length.

In general, the web length can be measured along the course of the web. This means that the web length corresponds to the path along the web 11 between two node points 13. Alternatively, the web length can also correspond to the direct distance between two node points 13, i.e. can be considered as an airline between two node points 13.

Particularly preferably, provision is made that the holding portion 22d extends along the entire length of the rectilinear area of the web 11. In particular, the holding portion 22d can be connected linearly to the web 11 along the entire length of the rectilinear area of the web 11. The holding portion 22d has, analogously to the rectilinear area of the web 11, a length corresponding to at least 10%, in particular at least 20%, in particular at least 30%, in particular at least 40%, in particular at least 50%, in particular at least 60%, in particular at least 70%, in particular at least 80%, in particular at least 90% of the total web length. It is also possible that the holding portion 22d extends beyond the rectilinear area of the web 11. The holding portion 22d can, for example, extend into the curved portions of the web 11. Moreover, the holding portion 22d can be connected in parts or sections to the rectilinear portion of the web 11. The holding portion 22d can extend as a whole over a part of the rectilinear portion of the web 11.

In the illustrative embodiment according to FIG. 19, the flap 21 has a single flap wing 24a, which comprises a holding portion 22d, said holding portion 22d being connected to the rectilinear area of the web 11. If several flaps 21 are provided about the circumference of the wall 10, it is preferred that the flaps 21 are oriented in the same way. The flaps 21, in particular adjacent flaps 21, thus have substantially the same longitudinal orientation. This ensures that the flaps 21 overlap each other during the transition of the wall 10 to the compressed state, i.e. they slide in a substantially flush manner on the circumference of the wall 10. A deviating movement of the flaps 21 in the radial direction relative to the tubular wall 10 is thus avoided. It is also possible for the flap 21 to be adapted in such a way that, during the compression of the wall 10, the flap 21 folds into the cell 12 or folds radially outward relative to the tubular wall 10 or generally deforms.

FIG. 14 shows another illustrative embodiment, in which the flap 21 can comprise a structuring. In particular, provision is made that the flap 21 has a pore structure 28 or perforation. Generally, the pore structure or perforation is formed by openings in the membrane 20, said openings being arranged in a pattern. Alternatively, the flap 21, in particular a surface of the flap 21, can have a fluted structure or a fleece structure. In general, the structuring of the flap 21 promotes endothelialization. The structuring is provided particularly for flaps 21 which are arranged on the outer circumference 14a of the wall 10. The structuring is in this case arranged on a radially outer face of the flap 21. Preferably, the structuring is provided on at least those flaps 21 which, during use, come into contact with a vessel wall 40. It is possible for medicaments to be incorporated into the structuring.

FIG. 15 shows a detail of a tubular wall 10 of a medical device according to another preferred illustrative embodiment, wherein several cells 12 are shown that each have a flap 21. The flaps 21 are structured at least on the surface. The structuring can also comprise a pore structure 28 or perforation. This means that the flap 21 can be structured all the way through, in particular can be interrupted by openings.

The cells 12, or the webs 11 forming the cells 12, are interconnected at node points 13. The flaps 21 are each connected to the webs at the node points 13. Thus, in the illustrative embodiment according to FIG. 15, the first ends 22a of the flaps 21 are coupled to the webs 11 directly in the area of or at the node point 13. This means that no fold opening 29 is provided in the illustrative embodiment according to FIG. 15. The flaps 21 each overlap the associated cell 12. This means that in each case the second end 22b of the flap 21 protrudes past the web 11 arranged opposite the first end 22a of the cell 12.

As regards its mode of function during the transition from the expanded state to the compressed state of the wall 10, the illustrative embodiment according to FIG. 15 differs from the other illustrative embodiments. In particular, in the medical device according to FIG. 15, provision is made that the flaps 21 overlap each other in the manner of roof tiles in the compressed state. Since the flaps 21 are connected by the respective first end 22a at the node point 13 to the supporting structure, namely the webs 11, it is thus ensured that the wall 10, in the compressed state, adopts a relatively small cross-sectional diameter.

In particular, a deformation, particularly a folding of the flap 21 into the cell 12, or a stretching of the flap 21, is avoided during the compression of the tubular wall 10. The flap 21 slides on the tubular wall 10 during the compression.

The tubular wall 10 according to FIG. 15 comprises at least a first row 12a of cells 12 and a second row 12b of cells 12. The first and second rows 12a, 12b each extend in the circumferential direction over the wall 10. The first row 12a and the second row 12b are offset in the longitudinal direction of the wall 10. This means that the first node points 13a of the second row 12b are in alignment or identical with the second node points 13b of the second row 12b in the circumferential direction. In particular, the second node points 13b of the first row 12a at the same time form the first node points 13a of the second row 12b. In the compressed state of the wall 10, the flaps 21 of the first and second rows 12a, 12b overlap each other in the circumferential direction. This means that a first flap 21a of the first row 12a overlaps another first flap 21a of the first row 12a in the circumferential direction. At the same time, a second flap 21b of the second row 12b overlaps another second flap 21b of the second row 12b in the circumferential direction.

In the expanded state of the wall 10, the first flaps 21a of the first row 12a are offset in relation to the second flaps 21b of the second row 12b in the circumferential direction of the wall 10. Therefore, the first flaps 21a of the first row 12a each overlap two second flaps 21b of the second row 12b in the compressed state of the wall 10. It is also possible that the first flap 21a of the first row 12a overlaps a second flap 21b of the second row 12b and at the same time, in another second flap 21b of the second row 12b adjacent to the second flap 21b in the circumferential direction, overlaps the first flap 21a of the first row 12a. Overall, provision is therefore made that the flaps 21 overlap one another in the manner of roof tiles in the circumferential direction of the wall 10.

Particular and preferred possible uses of the medical device are described below with reference to FIGS. 3 to 9:

A valve function is expediently achieved by the flexible flap. In general, the supporting structure of webs 11 is provided with a membrane which, in the radial direction relative to the longitudinal axis of the tubular wall 10 or generally of the medical device, has valve-like elements. The valve-like elements are formed by the flaps 21. The valve function can be used particularly advantageously in the area of blood vessels. Here, the tubular wall 10 is designed as the lattice structure of a stent or flow diverter. A flow of blood in the radial direction through the tubular wall 10 is permitted by the flaps 21 that can be actuated like valves. This can be advantageous in the area of perforations, preferably within aneurysms, and/or bifurcations or generally tributary vessels 42. The flap 21 can generally be adapted in such a way that the cell 12 is freed to permit a through-flow when a pressure gradient is established between the axial hollow channel 30 of the medical device and a space outside the tubular wall 10. If the pressure difference between the axial hollow channel 30 and the area outside the tubular wall 10 is comparatively small or equal to zero, the closed flap 21 forms a protection against detachment of particles, for example in the area of vulnerable plaques. In the closed position, the flap 21 can also serve as flow diverter. For example, the flap 21 assumes the closed position when, after successful treatment of an aneurysm 50, the blood flow within the aneurysm 50 is stopped. The same applies when the flap 21 bears directly on a vessel wall 40.

Figure 3:
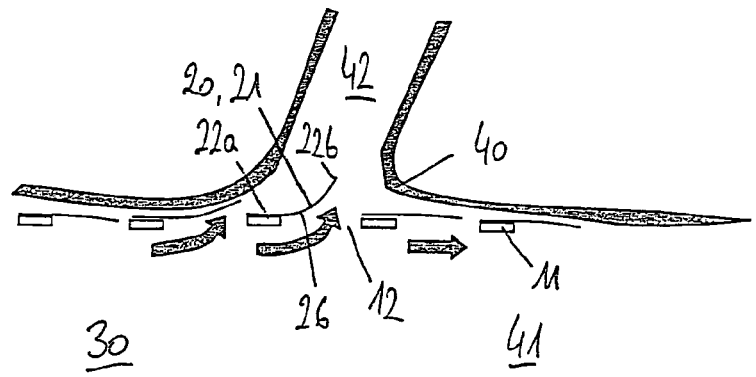
Figure 3:
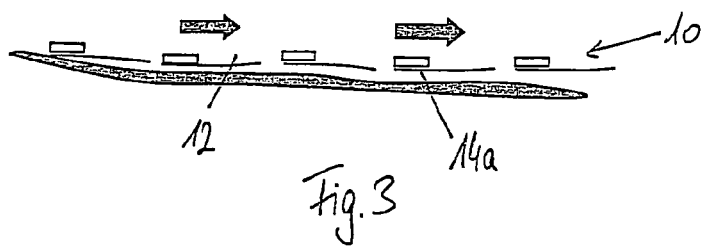
Figure 4:
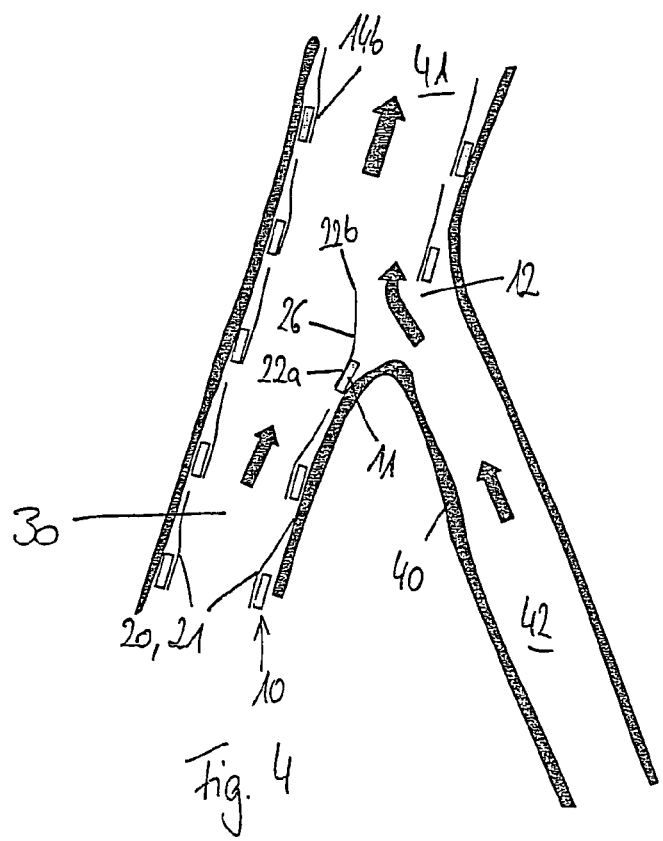
Figure 5:
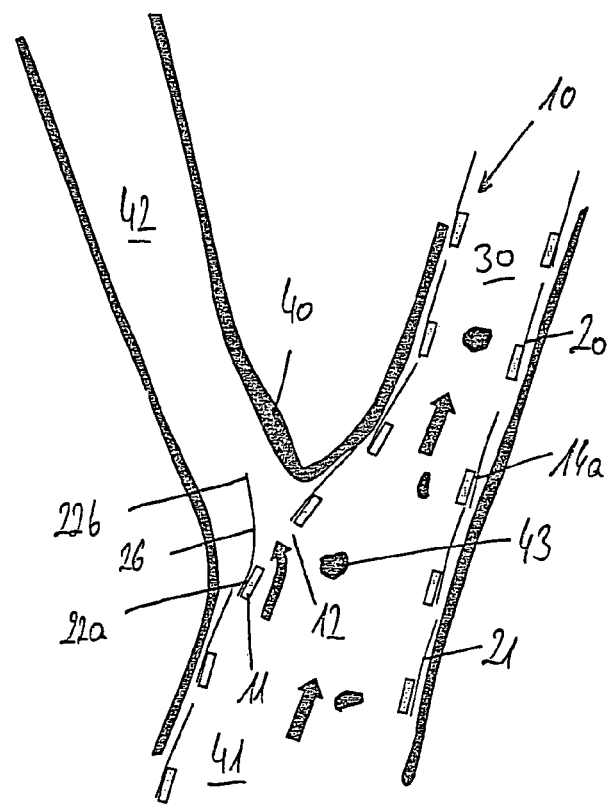

In FIGS. 3 to 9, the direction of the flow of fluid or specifically of the flow of blood is indicated by arrows. FIGS. 3 to 5 show the advantageous use of the medical device in the area of bifurcations. The bifurcation has a main vessel 41 and a tributary vessel 42. In the illustrative embodiment according to FIG. 3, body fluid flows from the main vessel 41 into the tributary vessel 42. Some of the flow of fluid from the main vessel 41 is thus branched off into the tributary vessel 42. It is particularly advantageous if the medical device used in this area has flaps 21 arranged on the outer circumference 14a of the wall 10. The flaps 21 are preferably oriented in such a way that the free second ends 22b of the flaps 21 point in the direction of the main flow of fluid. In the area of the branching to the tributary vessel 42, the flow of fluid causes the flaps 21 to move from the closed position to the open position, such that body fluid can flow from the main vessel 41 into the tributary vessel 42. For this purpose, the second end 22b of the flap 21 is deflected radially outward in the open position. It is also possible that the free second end 22b is deflected radially inward, for example in order to permit a return flow from the tributary vessel 42 into the main vessel 41. Such a return flow is preferably blocked by means of the flap 21 being adapted in such a way that a deflection is possible only in one direction. For example, the flap 21 can overlap the cell 12 such that, in the closed position, the second end 22b lies on the webs 11 of the cell 12. A deflection of the second end 22b in a radially inward direction relative to the tubular wall 10 is thus prevented. This does not exclude the possibility that the one-way valve function is achieved if the flap 21 is deflectable in both directions. The one-way valve function can also be achieved, for example, by the physiological flow conditions.

In the illustrative embodiment according to FIG. 4, the flaps 21 are arranged on the inner circumference of the tubular wall 10. This embodiment is particularly suitable for supporting vessels in the area of bifurcations in which a flow of fluid runs from a tributary vessel 42 into a main vessel 41. The flow of fluid from the tributary vessel 42 thus impacts the medical device from a radially outward direction and is intended to be conveyed into the hollow channel 30. The flaps arranged on the inner circumference 14b permit a simple radially inward deflection of the second ends 22b, such that the flow of fluid can pass from the tributary vessel 42 into the main vessel 41. It is also possible that the flaps 21 are arranged on the outer circumference 14a of the tubular wall 10 and are deflected inward in the open position. Analogously to the configuration according to FIG. 3, it is possible that a deflection of the flaps 21 is blocked in one direction, for example by means of the flap 21 overlapping the associated cell 12. As can be clearly seen in FIG. 4, the webs 11 are arranged on the outer circumference of the tubular wall 10. This results in a surface structure on the outer circumference 14a, which promotes endothelialization of the entire medical device. The webs 11 can also serve as holding elements that engage in the vessel wall 40.

The illustrative embodiment according to FIG. 5 corresponds substantially to the illustrative embodiment according to FIG. 3, wherein the flaps 21 are arranged on the outer circumference 14a of the wall 10 and permit a flow of fluid from a main vessel 41 into a tributary vessel 42. FIG. 5 also shows that the medical device can be advantageously used such that particles in the flow of fluid, for example thrombus constituents, can be conveyed into a specific vessel. The coverage of the tributary vessel 42 by the flexible membrane 20, in particular by the flaps 21, has the effect that the particles 43 carried in the flow of fluid are conveyed through the axial hollow channel 30. A flow of particles 43 into the tributary vessel 42 is avoided.

Figure 6:
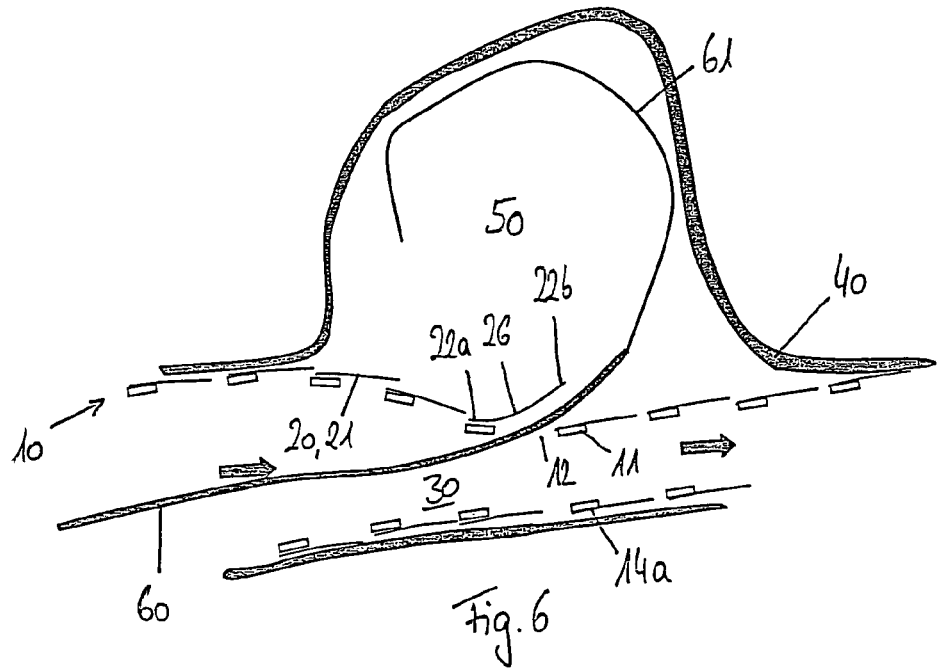
Figure 7:
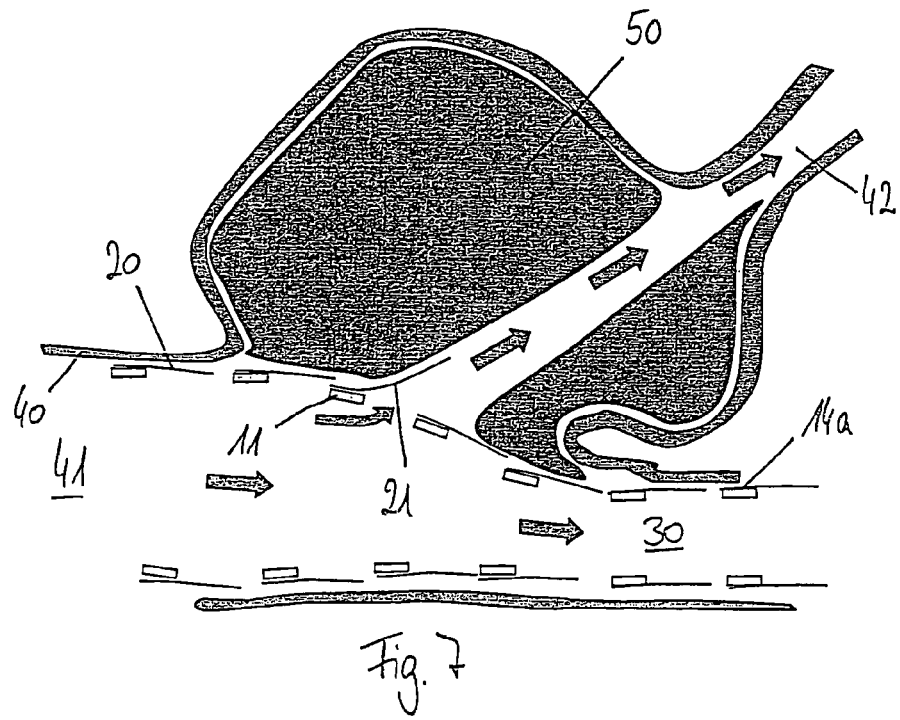

Another preferred use of the medical device is in the treatment of aneurysms 50, as is shown by way of example in FIGS. 6 and 7. For this purpose, provision is advantageously made that at least the area of the tubular wall 10 facing toward the aneurysm 50 is provided with the flexible membrane 20. The flexible membrane 20 or the flaps 21 close off the opening of the aneurysm 50, such that a flow of blood into the aneurysm 50 is suppressed. This corresponds substantially to the function of known flow diverters. In addition, the flexible membrane 20, particularly the flaps 21, permits the insertion of a catheter 60 through the cell 12 into the aneurysm 50, the flap 21 being moved from the closed position to the open position by the advancing force of the catheter 60. In this way, it is possible to additionally fill the aneurysm 50 with a coil 61, in order to achieve short-term embolization.

The use of the medical device is particularly expedient in aneurysms located in the area of bifurcations, as shown in FIG. 7. In bifurcation aneurysms of this kind, the flexible membrane 20 can assume a dual function. Part of the membrane 20, in particular of the flaps 21, arranged in the area of the aneurysm 50 advantageously closes off the inflow of blood into the aneurysm 50. At the same time, at least one flap 21 can ensure a flow of blood from the main vessel 41 into the tributary vessel 42, with formation of a flow passage 44 that extends through the aneurysm 50.

Figure 8:
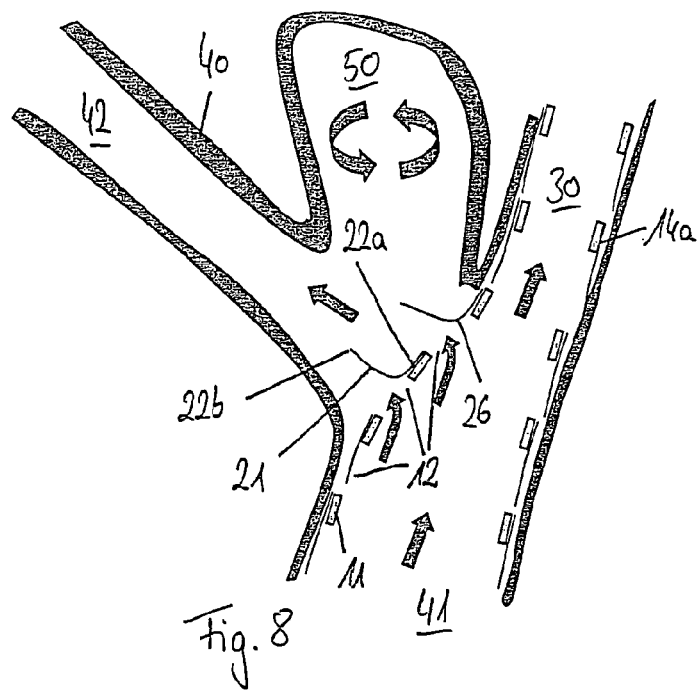

This advantageous property is also evident in the illustrative embodiment according to FIG. 8. In terms of its design, the medical device according to FIG. 8 corresponds substantially to the illustrative embodiment according to FIG. 3, but the medical device according to FIG. 8 is inserted into the vessel counter to the direction of flow. This means that the second free ends 22b of the flaps 21 point counter to the direction of the flow of fluid. As is indicated by the arrows in FIG. 8, this has the effect that body fluid can flow from the main vessel 41 into the tributary vessel 42 through the flaps 21 in the area of the bifurcation. In the configuration shown in FIG. 8, the flap 21, in the open position, prevents a direct inflow of the body fluid into the aneurysm 50.

Figure 9:
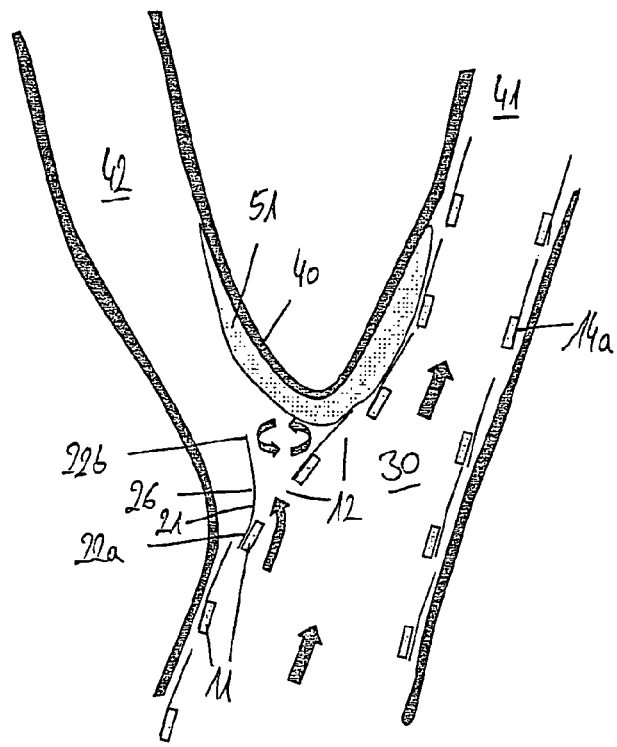

FIG. 9 shows the advantageous treatment of a stenosis in the area of a bifurcation, with the aid of the medical device. Here, the flaps 21, oriented in the direction of flow, permit a branching flow of fluid from the main vessel 41 into the tributary vessel 42. Between the main vessel 41 and the tributary vessel 42, a stenosis has formed in a common vessel wall 40. A return flow of the body fluid from the tributary vessel 42 into the main vessel 41 can be prevented by the flap 21. This avoids stenosis particles passing from the stenosis 51 into the main vessel 41.

Figure 16A:
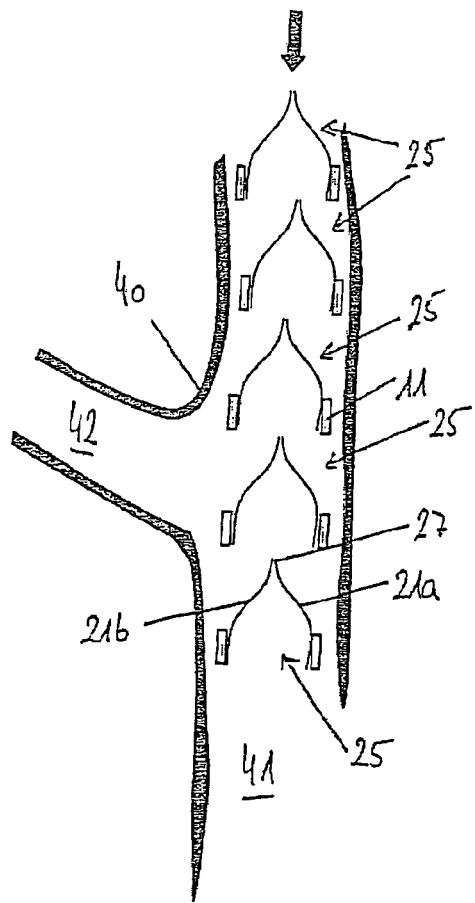
Figure 16B:
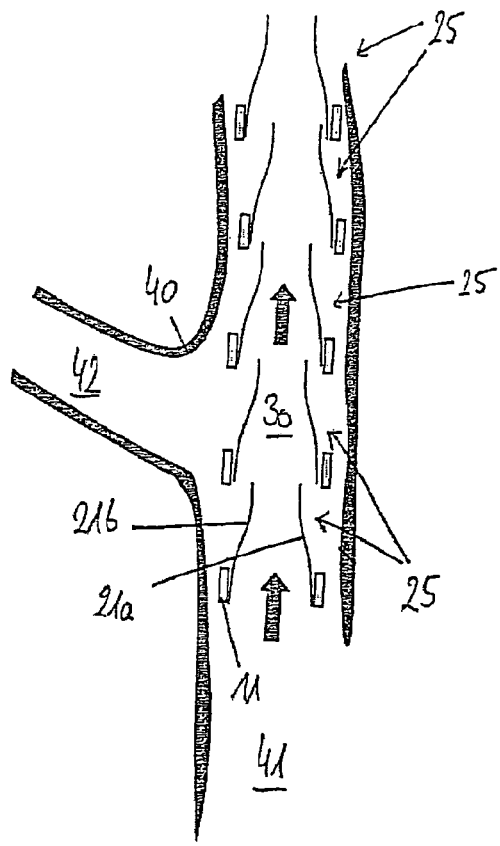

FIGS. 16a and 16b show an advantageous embodiment of the additional aspect of the invention in which the flaps 21 are arranged in such a way that, in the closed position, they close the axial hollow channel 30, as is shown in FIG. 16a. The tubular wall 10 of the medical device comprises a support structure of webs 11, which define the shape of the hollow channel 30. At least two flexible membranes 20, which are spaced apart from each other in the axial direction of the hollow channel 30, are arranged on the inner circumference 14b of the wall 10. The flexible membranes 20 each form a multiple flap 25 which, in the illustrative embodiment according to FIGS. 16a and 16b, in each case comprises two flaps 21. According to FIGS. 16a and 16b, five membranes 20 are provided, which each form a multiple flap 25 with two flaps 21. The multiple flap 25 can also comprise more than two flaps 21, in particular three flaps 21. The flaps 21 each have a curvature, which is S-shaped in cross section. The free second ends 22b of the flaps 21 of a multiple flap 25 touch in the closed position. The multiple flap 25 thus forms a substantially tear-shaped longitudinal profile. In the closed position, the second ends 22b of the flap 21 form a tip 27 of the multiple flap 25. The medical device is preferably oriented in the hollow vessel of the body in such a way that the tip 27 points in the main direction of flow. This has the effect that the multiple flap 25 opens automatically when a flow of fluid acts on it from the main direction of flow. By contrast, the multiple flap 25 closes automatically when a flow of fluid develops counter to the main direction of flow. In this way, a return flow of body fluid can be avoided.

The medical device according to the additional aspect of the invention can be used as a venous valve prosthesis. FIG. 16a shows the multiple flaps 25 in the closed position, the arrow indicating that a return flow of a body fluid, in particular blood, leads to the closure of the multiple flaps 25. The open position of the multiple flaps 25 is shown in FIG. 16b, where the arrows symbolize the flow of fluid in the main direction of flow. In the open position, the flaps 21 of the multiple flap 25 extend substantially on the inner circumference 14b of the wall 10.

In the illustrative embodiments according to FIGS. 16a and 16b, it is also possible for the flaps 21 to be adapted in such a way that the vessel is completely closed. For example, the flaps 21 can have a restoring force that prevents opening of the multiple flap 25 as a result of the flow of fluid.

Figure 17A:
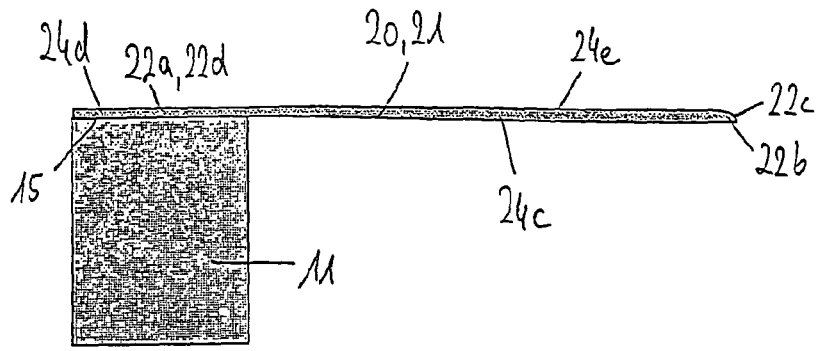
Figure 17B:
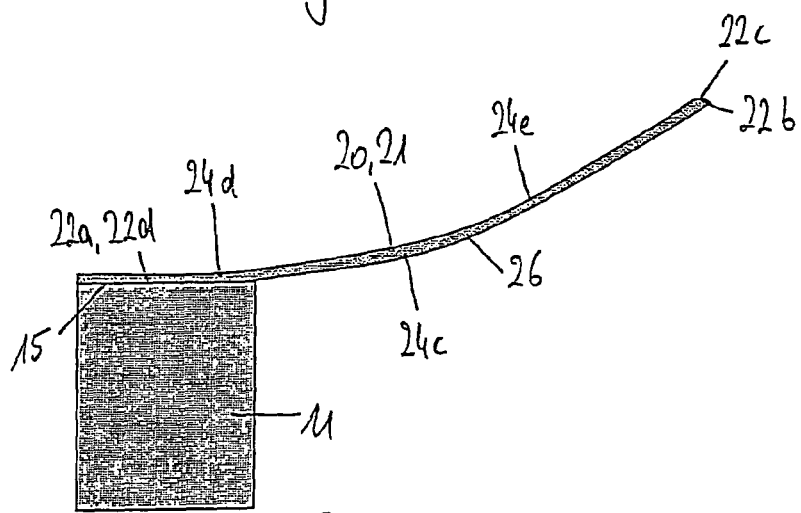
Figure 17C:
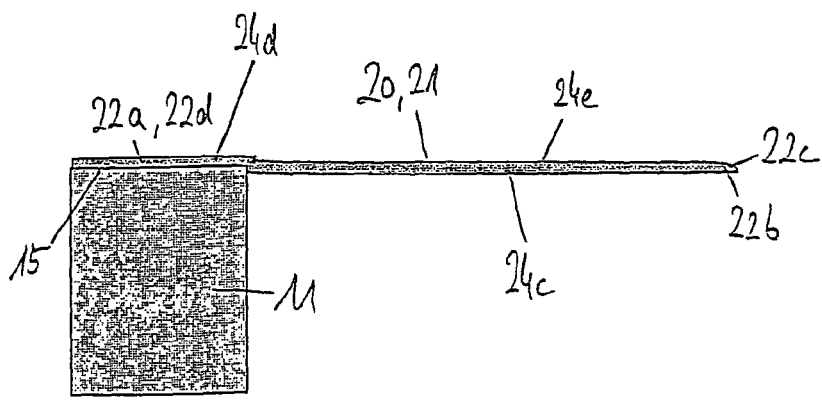

FIGS. 17a to 17c each show a preferred arrangement of the flap 21 on a web 11. In the closed position, the flap 21 extends along the wall 10. This means that the flap 21 is oriented substantially parallel to an outer edge 15 of the web 11. In the open position, as is shown in FIG. 17b, the second end 22b of the flap 21 is deflected relative to the first end 22a. The deflection takes place in a radial direction relative to the tubular wall 10. As a result of the deflection, the flap 21 forms a curvature 26. The curvature 26 can be dependent on the strength of the flow of fluid that passes through the cell 12 or is freed by the flap 21.

In connection with the additional aspect of the invention, FIG. 17a corresponds to the open position, and FIG. 17b to the closed position, of a preferred illustrative embodiment.

In general, the flap 21 can have a free portion 24c and a fixed portion 24d. The fixed portion 24d is connected firmly to the web 11. The free portion 24c extends across the cell 12 and forms the curvature 26 in the deflected state of the second end 22b. As is shown in FIG. 17c, the free portion 24c can be offset relative to the fixed portion 24d. This means that a step 24e forms between the fixed portion 24d and the free portion 24c. The free portion 24c is preferably offset into the wall 10. This means that the free portion 24c is offset starting from the outer circumference 14a in the direction of the inner circumference 14b and, conversely, starting from the inner circumference 14b in the direction of the outer circumference 14a of the wall 10. The outer face 24f of the free portion 24c is preferably aligned with the outer edge 15 of the web 11.

The medical device can be produced by an ablation method. An example of such an ablation method is described in the applicant's international patent application WO 2008/022799 A2 and is herewith fully disclosed by reference. Alternatively, the support structure of webs 11 and the membrane 20 can be produced separately and then connected to each other. The support structure and the membrane 20 can each be produced flat and connected to each other. In a further step, the support structure, together with the connected membrane 20, can be bent into the tube shape. The flexible membrane 20 can be produced in one piece and connected to the webs 11. It is also possible for several separately produced membranes 20 to be connected to a support structure of webs 11. The membrane 20, in particular the flaps 21, can be adhesively bonded to the webs 11 or welded thereto, in particular by laser welding or resistance welding.

Possible materials for the membrane 20 are plastics, in particular polyurethane. The flexible membrane 20 preferably comprises a metal alloy, particularly nitinol. The webs 11 can likewise be produced from a metal alloy, preferably nitinol. The webs 11 can be produced by a laser cutting method, for example. It is also possible to form the webs 11 by a sputtering method, in particular a sputtering/etching/sputtering method. The webs 11 or the tubular wall 10 and the membrane 20 can be produced from a tubular raw material or from a flat material. When a flat raw material is used, a further method step is carried out in which the tube shape is produced.

The flaps 21 can be produced by a laser cutting method in which the membrane 20 is correspondingly structured or cut. The membrane 20, in particular the flaps 21, can also be produced by a sputtering method and/or an etching method. Analogously to the production of the webs 11, the membrane 20, in particular the flaps 21, can be produced from a circular or a flat raw material. For example, the membrane 20 can be produced from a flat material, then rolled up and mounted onto an already tubular lattice structure of webs 11. The membrane 20 and the webs 11 can also be produced integrally. Suitable methods for this purpose are, for example, laser ablation methods, etching methods, in particular photochemical etching, or electrochemical machining.

With regard to other preferred production methods, reference is made to the German patent application which was filed at the same time by the applicant under the title "Medical implant" and of which the disclosure is hereby incorporated in full into the present application.

In the context of another production method for covers that overlap the lattice structure, the cover can be produced such that it extends only into an area within a cell. In this first production step, there is no overlapping. The overlapping of the cover with the lattice structure is obtained by the later deformation of the cell, for example by the compression of the cell in the circumferential direction. In this state, the rest state of the cell is fixed again, for example by heat treatment. The cell adopts its final geometry in the rest state. Therefore, in the rest state, the lattice structure or the stent has covers that overlap on the lattice structure. This production technique is easy to carry out and is suitable for all geometries in which the cover overlaps the lattice structure. With overlapping in the rest state, it is possible to prevent the film or the cover from bending into the cell during crimping.

With regard to the dimensions and materials of the flap 21, it will be generally noted that the expedient valve function is achieved both with a radially outward deflection of the flap 21 and also with a radially inward deflection of the flap 21. The flap 21 is in principle flexible, such that the flap 21 is radially deflectable or deformable, at least in one direction, from the plane of the tubular wall 10. The deformation or deflection can be inward and/or outward in relation to the tubular wall 10. The flexibility or deflectability of the flap 21 can be adapted in such a way that different rates of opening or degrees of opening of the flap 21 can be set. The flap 21 can be adapted in such a way that a preferred direction of opening is set. For example, the flap preferably opens in a preferred direction under the effect of a pressure gradient, irrespective of the direction in which the pressure gradient acts. Generally, the behavior of the flap 21 can be influenced by the arrangement of the flap 21 in relation to the webs 11 and by the positioning of the flap 21 on the outer circumference or the inner circumference of the tubular wall 10.

It is also possible that the flap 21 is flexible and active in such a way that the flap 21 adopts the open position even when external forces acting on the flap 21 are negligible. This is the case, for example, when the external forces acting on the flap 21 are barely measurable. The flexibility of the flap 21 can be adapted such that the flap 21 orients itself in the direction of the flow of fluid, wherein a return effect of the flap 21 on the flow of fluid is negligible. In particular, this avoids a situation where a return effect of the flap 21 on the flow of fluid leads to a pressure drop. It is still possible that a minimal and substantially barely measurable pressure drop arises through the friction of the fluid on the surface of the flap 21.

By means of the medical device, particles transported with the flow of fluid can be conveyed in a preferred direction through the flexible membrane 20, which forms at least one flap 21. This function is adjustable in particular through the dimension or materials or the mechanical properties of the flap 21. In particular, the flow or the flow component through the cell 12 can be adjusted by the rate of opening or the degree of opening of the flap 21. For example, with low through-flow rates of the flow of fluid, it is possible for small amounts of the body fluid, for example small amounts of blood, to supply distal tissue of the tributary vessel 42. By contrast, particles, in particular thrombus particles, are carried with the main flow and are therefore not transported through the cells 12 of the tubular wall 10. In this connection, the wall thickness of the flap 21 and the geometry of the flap 21 are adjustable parameters that accordingly influence the behavior of the flap 21.

It is possible that the rate of opening and the degree of opening can be modified depending on the load or the external forces acting on the flap 21, for example a pressure gradient. The same applies to the flexibility of the flap 21, which can likewise be modified depending on external forces acting on the flap 21. For example, if the medical device is used for the treatment of aneurysms, a central area of the medical device, particularly the area covering the aneurysm, can be provided with flaps 21 that have a relatively high degree of stiffness, in order to reliably block a flow of fluid into the aneurysm. By contrast, at the axial ends of the medical device or of the tubular wall 10, the flaps 21 can have increased flexibility, in order to permit the flow of blood into tributary vessels 42.

By contrast, in the treatment of stenoses, for example in the area of the carotid arteries, a high degree of flexibility of the flaps 21 in the central area of the tubular wall 10 may be advantageous. In this way, the flaps 21 in the central area of the tubular wall 10 have a relatively high rate of opening or a relatively high degree of opening, so as to permit a flow of blood through a tributary vessel 42, in particular the external or internal carotid artery. By contrast, at the axial ends of the tubular wall 10, the flaps 21 can have a relatively high degree of stiffness, in order to cover and protect the stenosis.

The flexibility and/or other properties of the flaps 21 can generally change in the longitudinal direction or circumferential direction of the tubular wall 10. For example, the medical device can have an area that comprises flaps 21 with first flap properties. Lying radially opposite this, another area can be provided that comprises flaps 21 with second flap properties. For the treatment of aneurysms, it is advantageous if the first flap properties bring about an increased flexibility of the flaps 21 and the second flap properties bring about an increased stiffness of the flaps 21. Generally, it is also possible that the rate of opening or the degree of opening of the flaps 21 can be adjusted by the size, i.e. the planar extent, of the flap 21.

Figure 20A:
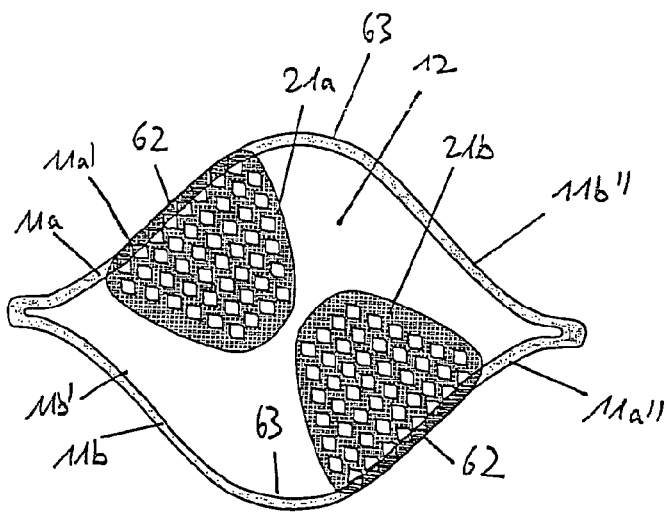
FIG. 20a shows a detailed view of a multiple flap of a medical device according to the invention, in another preferred illustrative embodiment and in the expanded state.
Figure 20B:
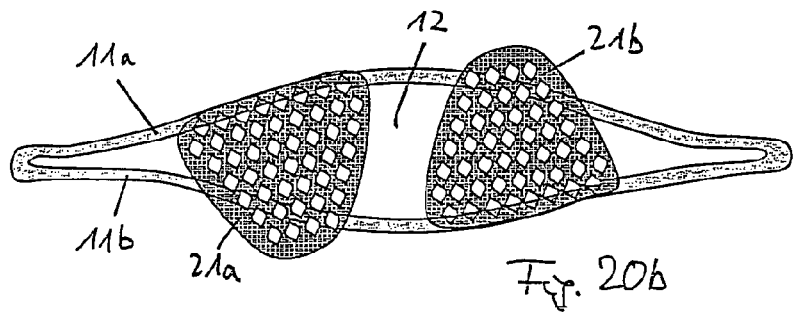
FIG. 20b shows the illustrative embodiment from FIG. 20a in the compressed state.

In the illustrative embodiment according to FIGS. 20a and 20b, provision is made that a cell 12 has two flaps 21a, 21b which, in an expanded state of the cell 12, are arranged opposite each other (FIG. 20a) and, in a compressed state of the cell 12, are arranged laterally alongside each other (FIG. 20b). The mutually opposing position of the flaps 21 means that the two second free ends 22b of the flaps 21a, 21b are arranged opposite each other. The second free ends 22b can be arranged directly opposite each other, in particular substantially in alignment, or can be arranged opposite each other and offset in relation to each other, in particular with offset longitudinal axes of the flaps 21a, 21b. The second ends 22b of the two flaps 21a, 21b can be arranged at approximately the same height or spaced apart from each other (FIG. 20a) or slightly overlapping. The second ends 22b of the two flaps 21a, 21b are at a distance from the first end 22a of the respective other flap 21a, 21b.

In the position in which the flaps are arranged laterally alongside each other (FIG. 20b), those sides of the flaps 21a, 21b that extend between the first and second ends 22a, 22b are arranged alongside each other. The second ends 22b of the two flaps 21a, 21b are arranged approximately at the same height as the first end 22a of the respective other flap 21a, 21b. The difference between the compressed state and the expanded state is generally that the second ends 22b of the two flaps 21a, 21b, in the expanded state, are arranged farther away from the first ends 22a of the two flaps 21a, 21b, in the longitudinal direction of the flaps 21a, 21b, than in the compressed state. Moreover, the second ends 22b of the two flaps 21a, 21b are arranged opposite each other in the longitudinal direction in the expanded state (spaced apart or overlapping or at the same height) and are offset alongside each other in the compressed state.

The flaps 21a, 21b are each secured on a straight portion 62 of the webs 11a, 11b located between the node points and the curved portions 63 of the cell in the expanded state (FIG. 20a). The flaps 21a, 21b are each provided on substantially parallel web portions 11a', 11a" of the first and second webs 11a, 11b. It is also possible to provide the flaps 21a, 21b, turned through 90°, on their two parallel web portions 11b', 11b". With this arrangement, the crimpability of the structure is improved and, in addition, large coverage of the cells is achieved.

Figure 20C:
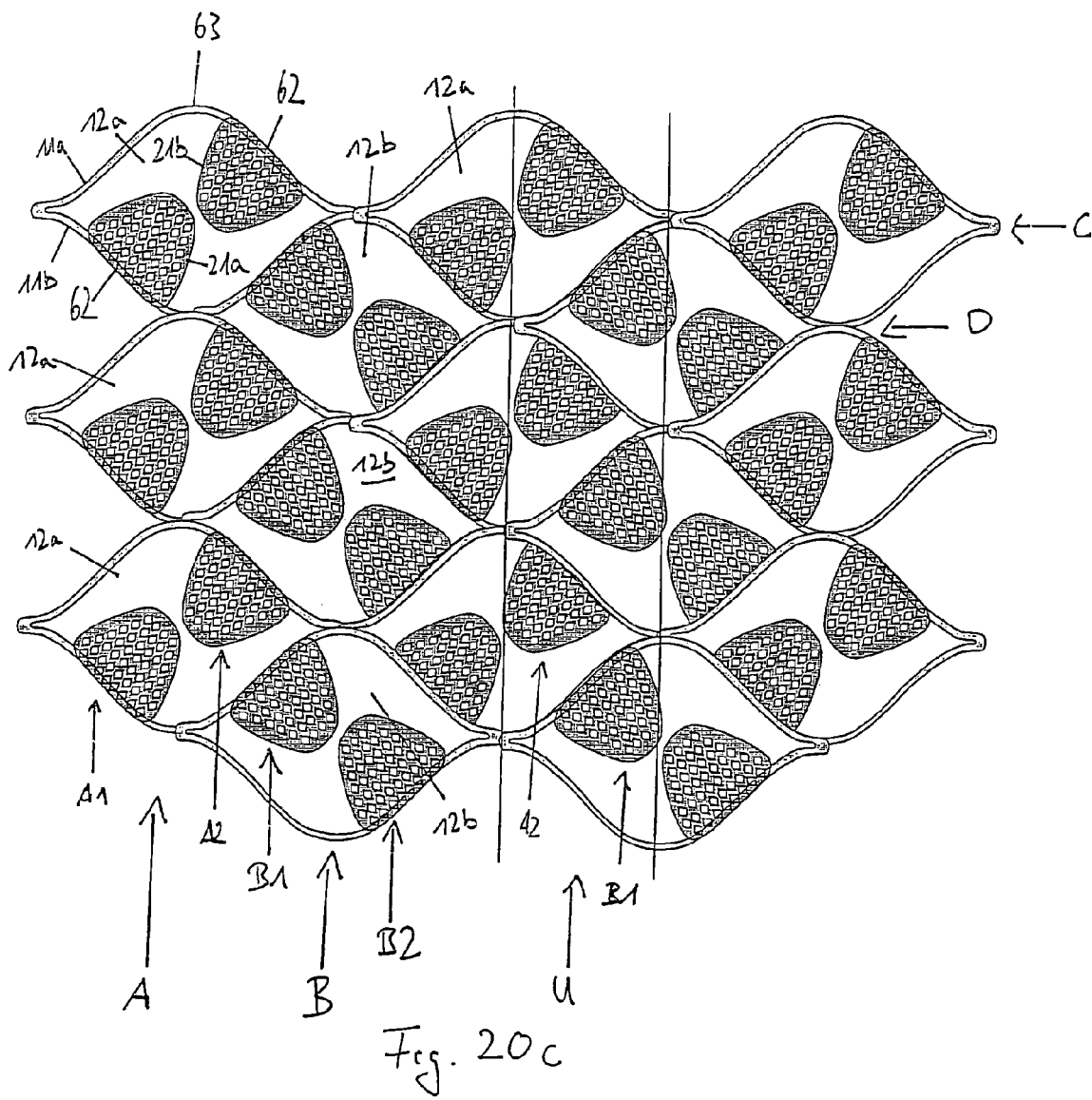
FIG. 20c shows a cutout from a lattice structure with cells according to the illustrative embodiment in FIG. 20a, and FIG. 21 shows a detailed view of a flap of a medical device according to the invention in another preferred illustrative embodiment, with a perforation extending as far as the web.

FIG. 20c shows the arrangement of a plurality of cells 12 which are designed according to FIG. 20a. If, as is shown in FIG. 20c, a plurality of flaps 21 are provided over the circumference of the wall 10, it is preferable that the flaps 21 have a similar orientation. The flaps 21, in particular adjacent flaps 21, thus have substantially the same longitudinal orientation. It will be specifically noted that the flaps 21a, 21b of a cell 12 are differently oriented, as is disclosed in FIGS. 20a and 20c and in the associated description. This results in the following arrangement pattern.

The two flaps 21a, 21b of a cell 12 are provided in different arrangements, in particular in two different arrangements. The two arrangements differ in that the flaps 21a, 21b of different cells 12a, 12b are oriented inversely. Specifically, the flaps 21a, 21b of the first cells 12a are turned through 90° in relation to the flaps 21a, 21b of the second cells 12b. Other angles are possible.

As can be seen clearly in FIG. 20c, the first cells 12a are arranged in a segment A, and the second cells 12b are arranged in a further segment B, in the circumferential direction of the lattice structure (in FIG. 20c this corresponds to the vertical direction). The segments A, B each form first cell rows, which extend in each case in the circumferential direction of the lattice structure. Within the cell rows, the first and second flaps 21a, 21b in turn form rows A1, A2 and B1, B2 in the circumferential direction, wherein the first flaps 21a form the first rows A1, B1, and the second flaps 21b form the second rows A2, B2, of the segments A, B. The segments A, B are arranged one after the other in the longitudinal direction of the lattice structure, in particular directly one after the other. The first cells 12a of the segment A are offset in the circumferential direction in relation to the second cells 12b of the next segment B.

Segments C, D are arranged at different heights in the longitudinal direction of the lattice structure, which segments C, D are arranged as lines and each have cells with oriented flaps 21a, 21b. The arrangement of the flaps 21a, 21b corresponds to the arrangement according to FIG. 20a, including the inversely oriented flap arrangement. The arrangement of the first and second cells 12a, 12b including the flap arrangement according to the segments A, B (circumferential direction) corresponds analogously to the arrangement of the first and second cells 12a, 12b including the flap arrangement according to the segments C, D (longitudinal direction).

The orientation of the flaps 21a, 21b to one another in a cell 12a, 12b, i.e. opposite each other in the expanded state and arranged alongside each other in the compressed state, is repeated in the other cells 12a, 12b of one and the same segment A or segment B. To this extent, the overall orientation of two flaps 21a, 21b of a cell 12 is identical per segment A or segment B. The orientation of the flaps 21a, 21b of the first cells 12a of one segment A is oriented differently, or turned, in particular through 90°, than the orientation of the flaps 21a, 21b of the second cells 12a of the next segment B in the longitudinal direction.

The same applies to the segments C, D extending in the longitudinal direction.

In the compressed state and/or during crimping, i.e. during the transition from the expanded state to the compressed state, the flaps 21b of the second row A2 of one segment A overlap the flaps 21a of the first row B1 of the next segment in such a way that, in the compressed state, the flaps 21a, 21b of the respective row A2, B1 are oriented in the same direction, in particular in the circumferential direction. It is also possible for flaps to partially overlap in the expanded state.

The arrangement of the flaps 21b of the second row A2 of one segment A and of the flaps 21a of the first row B1 of the next segment B can also result from the fact that the flaps 21b of the second row A2 of one segment A and the flaps 21a of the first row B1 of the next segment B have the same circumferential direction in the area indicated by U in FIG. 20c.

In the illustrative embodiment according to FIGS. 20a and 20b, the deformation of the flaps 21 is minimized by their being secured on the straight web portions.

The flaps 21a, 21b are designed such that they can slide on the webs. They are slidable. For this purpose, the flaps 21a, 21b are secured on an outer face or inner face of the webs, i.e. on a top face or bottom face of the webs. In addition, the wall thickness of the flaps 21a, 21b is smaller than the wall thickness of the webs. The wall thickness of the flaps 21a, 21b in relation to the wall thickness of the webs can be at most 50%, in particular at most 40%, in particular at most 30%, in particular at most 20%, in particular at most 10%, in particular at most 5%.

A further advantage of the flaps 21a, 21b is their retractability. For this purpose, the edges of the flaps 21a, 21b, in particular the front or proximal edges in the direction of retraction, are designed such that, in the compressed state of the lattice structure according to FIG. 20b, they are inclined at an angle in relation to a plane perpendicular to the central longitudinal axis of the device. Since the cell in the example according to FIG. 20b is stretched such that the webs extend almost parallel to the central longitudinal axis, the edges are inclined at an angle of more than 90° to the webs 11a, 11b. At other degrees of compression, in which the webs are deflected to a lesser extent, the plane perpendicular to the central longitudinal axis of the device is used as a reference for the angle of inclination of the edges. The angle of inclination in relation to the plane perpendicular to the central longitudinal axis of the device can be at least 10°, in particular at least 15°, in particular at least 20°, in particular at least 25°, in particular at least 30°, in particular at least 35°, in particular at least 40°, in particular at least 45°, in particular at least 50°, in particular at least 55°, in particular at least 60°.

In the expanded state, the edge angle is greater, specifically depending on the tilt angle, which describes the angle between the two webs 11a, 11b on the connector. The tilt angle is at least 60°, in particular at least 80°, in particular at least 90°, in particular at least 100°, in particular at least 120°.

In the illustrative embodiment according to FIG. 20b, the flaps 21a, 21b each overlap a single neighboring cell. It is possible that one flap 21a and/or the other flap 21b in each case overlaps at least one neighboring cell, in particular at least two neighboring cells, in particular at least three neighboring cells, in particular at least four neighboring cells, in particular at least five neighboring cells, in particular at least six neighboring cells.

Figure 21:
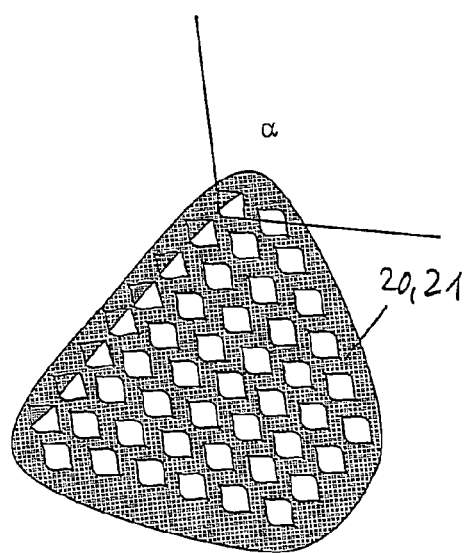

In the illustrative embodiment according to FIG. 21, an alternative or additional measure is described which serves to avoid or reduce the deformation of the cover and also permits the arrangement of the flaps on curved portions. The structure of the cover or of the flap, in particular the perforation, extends as far as the edge of the web 11a, on which edge the flap 21 is secured. The connection of the film or flap 21 to the web 11a is interrupted at several places. Upon stretching of the web 11a during crimping, and likewise upon curving thereof during expansion, the openings of the structuring or of the pore structure 28 open in the web area, such that the film or flap does not deform or deforms only inappreciably. In particular, the angle α of the cells of the perforation, or the shape of the slits, changes. The angle α should be as large as possible, specifically, as in the rest of the structuring, in particular at least 90°, in particular at least 120°, in particular at least 130°, in particular at least 140°, in particular at least 150°, in particular at least 160°, in particular at least 170°. The cells or openings of the perforation are preferably oriented with the course of the web 11a.

Provision is advantageously made that the flaps 21 comprise a plastic, in particular polyurethane. It is particularly preferable if the flaps 21 comprise a nickel-titanium alloy, in particular nitinol. A combination of a plastic and a nickel-titanium alloy is possible. For example, suitable composite materials can be used. Other possible materials include biodegradable materials, for example magnesium or magnesium alloys. Dissolution of the flaps may be desirable in some cases and accelerates endothelialization, if the acute function of the flaps is no longer needed. The whole structure or just the flaps can be partially or completely biodegradable. It is also possible to incorporate medicaments (genetic therapeutic agents, anticoagulants or other substances) within the biodegradable material, or on the surface thereof, or also in microstructures or nanostructures in the material.

The medical device can be produced by the following method, which comprises the steps of:
  making available a tube shape of the lattice structure;
  applying to the lattice structure a sacrificial layer comprising a photoresist and/or a sacrificial film;
  structuring the sacrificial layer, wherein a structure of connection points of the lattice structure, in particular web portions, is exposed;
  applying a cover layer to the sacrificial layer and the connection points in such a way that the cover layer is connected at the connection points to the lattice structure and forms a cover element, in particular a membrane or flap; and
  removing the sacrificial layer in order to form the cover element.

Regarding the details of the method, reference is made to the application which was filed on the same day by the applicant under the title "Medical implant and method for producing such an implant" and of which the disclosure is hereby incorporated in full into this application.

Other known production methods are also possible, for example the connection of the flaps to the webs by laser welding.

LIST OF REFERENCE SIGNS 10 wall
11 web
11a first web
11b second web
11a', 11a" web portions
11b', 11b" web portions
12 cell
12a first row
12b second row
13 node point
13a first node point
13b second node point
14a outer circumference 14b inner circumference
15 outer edge
20 membrane
21 flap
21a first flap
21b second flap
22a first end
22b second end
22c free edge
22d holding portion
22e inner edge
23 fold line
23a groove
23b gap
23c gap edge
24a first flap wing
24b second flap wing
24c free portion
24d fixed portion
24e outer face
25 multiple flap
26 curvature
27 tip
28 pore structure
29 fold opening
30 axial hollow channel
40 vessel wall
41 main vessel
41 tributary vessel
43 particle
50 aneurysm
51 stenosis
60 catheter
61 coil
62 straight portion
63 curved portion

The invention claimed is:

1. A medical device with a tubular wall made of webs, which delimit closed cells, and with a flexible membrane, which forms at least one flap, the flap comprising:
a first end connected to at least one first web of a cell, and
a free second end arranged opposite the first end in the longitudinal direction of the flap,
wherein the flap is configured to move between
a closed position, in which the flap extends along the tubular wall and at least partially closes the cell, and
an open position, in which the flap is radially deflected relative to the wall in order to free the cell in the manner of a valve;
wherein the flap is configured to move between the closed position and the open position in response to a pressure gradient between a space inside the tubular wall and a space outside the tubular wall and wherein in the closed position, the free second end of the flap protrudes into the cell, in particular is arranged inside the cell, or overlaps the cell.

2. The medical device as claimed in claim 1, wherein the cell has at least one first node point, which connects the first web to a second web, wherein the first web and the second web enclose an angle in the area of the node point, and the first end of the flap is connected to the first web and/or the second web in the vicinity, in particular in the area, of the node point.

3. The medical device as claimed in claim 1, wherein the first end of the flap is arranged on an outer circumference or an inner circumference of the tubular wall.

4. The medical device as claimed in claim 1, wherein the flap free second end has a curved free edge that is substantially omega shaped.

5. The medical device as claimed in claim 1, wherein the flap has a surface structuring, in particular a pore structure or a fluted structure or a fleece structure.

6. The medical device as claimed in claim 1, wherein the flap has a fold line, which extends at least in parts from the first end to the free second end.

7. The medical device as claimed in claim 6, wherein the fold line divides the flap into a first flap wing and a second flap wing.

8. The medical device as claimed in claim 7, wherein the first flap wing is connected to the first web of the cell, and the second flap wing is connected to the second web of the cell.

9. The medical device as claimed in claim 6, wherein the fold line comprises a groove and/or a gap.

10. The medical device as claimed in claim 9, wherein the gap separates the first flap wing at least in parts from the second flap wing.

11. The medical device as claimed in claim 9, wherein the gap separates the first flap wing completely from the second flap wing in such a way that the first flap wing is arranged spaced apart from the second flap wing.

12. The medical device as claimed in claim 1, wherein the flap is movable automatically from the closed position to the open position.

13. The medical device as claimed in claim 1, wherein the flap, in the closed position, extends in the longitudinal direction or in the circumferential direction of the tubular wall.

14. The medical device as claimed in claim 1, wherein the membrane has several flaps which, in the closed position, extend along the tubular wall.

15. The medical device as claimed in claim 14, wherein, at least in the compressed state of the tubular wall, in each case a free second end of a first flap overlaps at least one first end of a second flap connected to a web.

16. The medical device as claimed in claim 1, wherein a cell has two flaps which, in an expanded state of the cell, are arranged opposite each other and, in a compressed state of the cell, are arranged laterally alongside each other.

17. The medical device as claimed in claim 1, wherein, at least in an area of the first end of the flap, a pore structure, in particular a perforation of the flap, is formed which extends into an area of the first web, wherein the first end is connected in parts to the first web in such a way that the pore structure of the first end is deformable in parts where the first end is not connected to the first web.

18. A medical device, in particular a stent, with a tubular wall, which forms an axial hollow channel and has webs that delimit closed cells, wherein at least two flexible membranes are provided, which are arranged spaced apart from each other in the longitudinal direction of the axial hollow channel and each form a multiple flap, each multiple flap including at least two flaps arranged radially opposite in relation to a longitudinal axis of the axial hollow space and comprising:
a first end connected to at least one first web of a cell, and
a free second end arranged opposite the first end in the longitudinal direction of the flap,
wherein the multiple flap is configured to move between
an open position, in which the at least two flaps extend along the tubular wall, and
a closed position, in which the at least two flaps are radially deflected relative to the wall and protrude into the axial hollow channel in order to close the axial hollow channel in the manner of a valve.

19. The medical device as claimed in claim 18, wherein the free second ends of the flaps touch in the closed position.

\* \* \* \* \*